US005863741A

United States Patent [19]

Limper et al.

[11] Patent Number: 5,863,741

[45] Date of Patent: Jan. 26, 1999

[54] **METHOD FOR IDENTIFYING INHIBITORS OF CDC2 PROTEIN KINASE FROM *PNEUMOCYSTIS CARINII***

[75] Inventors: Andrew H. Limper; Edward B. Leof; Charles F. Thomas; Michael P. Gustafson, all of Rochester, Minn.

[73] Assignee: Mayo Foundation for Medical Education and Research, Rochester, Minn.

[21] Appl. No.: 874,347

[22] Filed: Jun. 13, 1997

[51] Int. Cl.$^6$ .......................... C12Q 1/00; G01N 33/53; C12N 9/12; C12N 9/00

[52] U.S. Cl. .......................... 435/7.6; 435/7.1; 435/194; 435/183

[58] Field of Search .......................... 435/7.6, 7.1, 194, 435/183

[56] References Cited

U.S. PATENT DOCUMENTS 4,683,195 7/1987 Mullis et al. .............................. 435/6

OTHER PUBLICATIONS

Thomas et al., "Identification of a Cell Division Cycle (cdc2) Homologue in *Pneumocystis Carinii*," *J. Euk. Micro*, vol. 43, No. 5 Sep.–Oct. 1996.

Thomas et al., "The *Pneumocystic Carinii* cdc2 Cell Division Cycle Homologue Exhibits Characteristics Protein Kinase Activity," *Chest*, 110:66S (1996).

Thomas et al., "Partial Cloning of the *Pneumocystis Carinii* Cell Division cycle (cdc2) Homologue Using Polymerase Chain Reaction," *J. Invest. Med.*, 44:397A (1996).

Thomas et al., "Evidence for a *Pneumocystis Carinii* Cell Division Cycle (cdc2) Homologue," *Am. J. Resp. Care Med.*, 153:A433 (1996).

J. Pines, "The cell cycle kinases," *Seminars in Cancer Biology*, 5:305–313 (1994).

Fleig et al., "Regulation of cdc2 activity in *Schizosaccharomyces pombe*: the role of phosphorylation," *Seminars in Cell Biology*, 2:195–204 (1991).

Sambrook et al., *Molecular Cloning*, second edition, Cold Spring Harbor Laboratory, Plainview, NY (Sections 7.39–7.52) (1989).

Dayhoff, et al., "A Model of Evolutionary Change in Proteins," *Atlas of Protein Sequencing and Structure*, vol. 5, Suppl. 3, pp. 345–352 (1978).

*Primary Examiner*—Karen Cochrane Carlson
*Attorney, Agent, or Firm*—Fish & Richardson, P.C., P.A.

[57] ABSTRACT

A nucleic acid and corresponding polypeptide that aids in the regulation of the cell cycle in *Pneumocystis carinii* is described. Antibodies generated against a unique carboxyl-terminus region of the polypeptide have specific binding affinity for *P. carinii* Cdc2 polypeptide and are beneficial in diagnosing and monitoring *P. carinii* infection in patients. Expression of *P. carinii* Cdc2 polypeptide in cdc2-mutant yeast and other cdc2-mutant organisms provides a useful model for studying the life cycle of *P. carinii* and for identifying novel therapeutics.

5 Claims, 16 Drawing Sheets

FIGURE 3A,I

```
gtcattttatatgataaatatgtttctctttctaacgatttctttgctataataatatc   60
attctgaatatcttctatcaataattctactttatttaaaagacagatctaaattaaaat  120
tgtgttacttttagatatataattgcgttctggccttataaaacccattattaataatct  180
tatttcttgatcatagaaatcgcatttaaatttatgtataaaatgtacttcctaaatctt  240
tttaaaacaaacctttttgtaatgaacatactgctgacaatttctggttcttataatacg  300
gattccatcccacgctcatgaccattatatagacgctatcgtcaccctctatcattactc  360
gaccccagccataataaattcctgttttgaatatagaaattttggaatatttcttctg    420
aaatatttgctaaaacatatcaatttatgtatattctttatttatacctgttggtatttc  480
caattcacttcttcctctaccatatcccttgaccacctatattttaacaatactaaaaa   540
aatactattaaaatttactaacttttcctttcaaataaataggataagggtattcaggac  600
ctgaatctggccctgaattatttctaattctatctccatatctgccattctacaaaaat   660
tttcaaatatctacaagactttaaacaactataacccttttaaacataaatatcaatatc  720
cctcgcttttcttacattaatgctgagcttttaagtaaaaatattgtctttctatatatt  780
atcttaccctctcactagaaaatatcacgtgacattgacataataacaacgtattttgaa  840
aataacgaggtaaactATGGAGCAATATCAGAGGTTAGAGAAGATTGGAGAAGgcataaa  900
                M  E  Q  Y  Q  R  L  E  K  I  G  E  G
aacctatatttatagagtttgcgcttatttgcatttaagGGACTTATGGAGTTGTTTATA  960
                                         T  Y  G  V  V  Y  K
AGGCCAAGGATCTTGAAAGTGGCACAATTGTAGCTCTTAAAAAAATCCGGTTAGAGGCAG 1020
 A  K  D  L  E  S  G  T  I  V  A  L  K  K  I  R  L  E  A  E
AAGATGAGGGAGTTCCTAGCACAGCAATTCGTGAAATATCTCTTTTGAAAGAAATGCACA 1080
 D  E  G  V  P  S  T  A  I  R  E  I  S  L  L  K  E  M  H  N
ATGATAATGTCGTAAGgtatcatttgctgtatttttttcacggggttttatgggtca    1140
 D  N  V  V  R
attagACTTTTGAATATTATTCATCAGGAATCACGTCTATATCTTGTTTTTGAAgtaggt 1200
     L  L  N  I  I  H  Q  E  S  R  L  Y  L  V  F  E
ttcttttcttttcatgaatgtttctcatttgttgtattagTTTCTTGATCTTGgtaatt  1260
```

FIGURE 3A,2

```
                                                F   L   D   L   D
cttatatatatatacataatatatatatatattcatatattatgttagATTTGAAAAAAT  1320
                                                   L   K   K   Y
ATATGAATAGTATTCCAAAAGACATGATGCTTGGAGCTGAAATGATCAAAAAATTTATGT  1380
 M  N  S  I  P  K  D  M  M  L  G  A  E  M  I  K  K  F  M  S
CTCAACTTGTATCAGGTGTTAAATATTGTCATTCTCATCGTATTCTTCATCGTGACTTGA  1440
 Q  L  V  S  G  V  K  Y  C  H  S  H  R  I  L  H  R  D  L  K
AGCCCCAAAATCTTCTTATTGATCGAGAAGGAAATCTTAAACTTGCTGATTTCGGGCTTG  1500
 P  Q  N  L  L  I  D  R  E  G  N  L  K  L  A  D  F  G  L  A
CTCGGGCATTTGGTGTTCCTTTACGTGGTTATACTCATGAGGTTGTTACACTTTGGTATC  1560
 R  A  F  G  V  P  L  R  G  Y  T  H  E  V  V  T  L  W  Y  R
GTGCTCCAGAAGTTCTTTTAGGTGGTCGACAATATGCAACAGCACTTGATATTTGGAGCA  1620
 A  P  E  V  L  L  G  G  R  Q  Y  A  T  A  L  D  I  W  S  I
TTGGATGTATTTTTGCTGAAATGGCTACAAAAAAACCGTTATTTCCAGGCGATTCTGAAA  1680
 G  C  I  F  A  E  M  A  T  K  K  P  L  F  P  G  D  S  E  I
TTGATGAAATATTCAGAATATTTAGgtcaagtttctgggtattaagtatatagtttattt  1740
 D  E  I  F  R  I  F  R
atttttcagAATATTAGGAACACCTGATGAAAATTCTTGGCCTGGTATTACATCATATCC  1800
          I  L  G  T  P  D  E  N  S  W  P  G  I  T  S  Y  P
TGATTTTAAAGCAACTTTTCCCAAATGGTCACCAAAAAATCTTGGAGAATTAATTACAGA  1860
 D  F  K  A  T  F  P  K  W  S  P  K  N  L  G  E  L  I  T  E
ACTTGATAGTGATGGAATAGATTTATTACAGgttttctatttacaatatagattattaaa  1920
 L  D  S  D  G  I  D  L  L  Q
aaataacaatgataactatgtagAAATGTCTCAGATATTATCCTGCTGAACGTATTAGTG  1980
                         K  C  L  R  Y  Y  P  A  E  R  I  S  A
CAAAAAAGGCTCTCGATCATCCATATTTTGATGATTTCATTAATCTCAATAGATCTAATG  2040
 K  K  A  L  D  H  P  Y  F  D  D  F  I  N  L  N  R  S  N  V
```

```
TGGTGCTAtagtttttatcattggtcattatataatttaaggtatttatatcaacttaa    2100
  V  L  *
tttcttctttttaacctaatagatctttaattttaaaaattgtctattataaataataga    2160
taagtaaatatctttgtaaatgattttcgcagatattgtataactatattggctataaaa    2220
ttcattcaattgattcataatttaaatacattgtaatattaaattaacatttctttaaat    2280
atctttatgacagtattttccggatatatttgataatttgcttataaaacatatgatttt    2340
tagataaatatttaacagccgtatttaacagagagattcaaccaaaagggttctattaag    2400
ctataaagtctatttgatatctaaatttgaaaaactatttaataataaattgtcattta    2460
aaaatgtccagtatttcagagagaaagatggatataaagagcttagcaggagcatctggt    2520
cctggatattcagatgtgtctttaaaatgcagaaaatgtaaaagttatgaggaaatattg    2580
gataataatgagccatctcaaaaacaagccaataatgacccagaaaaaaggaatatttct    2640
ggttctttgaaagacatcatagagaaagaggctatagtcagaattgctatgcctgcaga    2700
tcttcagtttccccaaaatctcatcaaatgacgagatttaatgaacg               2747
```

```
Pc Cdc2   ....MEQYQR LEKIGEGTYG VVYKAKDL.. .ESGTIVALK KIRLEAEDEG
Ca Cdc2   .MVELSDYQR QEKVGEGTYG VVYKALDTK. .HNNRVVALK KIRLESEDEG
Sc Cdc2   MSGELANYKR LEKVGEGTYG VVYKALDLRP GQGQRVVALK KIRLESEDEG
Ac Cdc2   ....MENYQK IEKIGEGTYG VVYKARDL.. THPNRIVALK KIRLEAEDEG
En Cdc2   ....MENYQK IEKIGEGTYG VVYKAREL.. THPNRIVALK KIRLEAEDEG
Sp Cdc2   ....MENYQK VEKIGEGTYG VVYKARH... KLSGRIVAMK KIRLEDESEG
Rn Cdc2   ....MEDYIK IEKIGEGTYG VVYKGRH... RTTGQIVAMK KIRLESEEEG
Hs Cdc2   ....MEDYTK IEKIGEGTYG VVYKGRH... KTTGQVVAMK KIRLESEEEG
Hs Cdk2   ....MENFQK VEKIGEGTYG VVYKARN... KLTGEVVALK KIRLDTETEG
Os Cdc2   ....MEQYEK EEKIGEGTYG VVYRARD... KVTNETIALK KIRLEQEDEG

Pc Cdc2   VPSTAIREIS LLKEMHND.. ..NVVRLLNI IHQES.RLYL VFEFLDLDLK
Ca Cdc2   VPSTAIREIS LLKEMKDD.. ..NIVRLYDI IHSDSHKLYL VFEFLDLDLK
Sc Cdc2   VPSTAIREIS LLKELKDD.. ..NIVRLYDI VHSDAHKLYL VFEFLDLDLK
Ac Cdc2   VPSTAIREIS LLKEMHDP.. ..NIVRLLNI VHADGHKLYL VFEFLDLDLK
En Cdc2   VPSTAIREIS LLKEMNDP.. ..NIVRLLNI VHADGHKLYL VFEFLDLDLK
Sp Cdc2   VPSTAIREIS LLKEVNDENN RSNCVRLLDI LHAES.KLYL VFEFLDMDLK
Rn Cdc2   VPSTAIREIS LLKELRHP.. ..NIVSLQDV LMQDS.RLYL IFEFLSMDLK
Hs Cdc2   VPSTAIREIS LLKELRHP.. ..NIVSLQDV LMQDS.RLYL IFEFLSMDLK
Hs Cdk2   VPSTAIREIS LLKELNHP.. ..NIVKLLDV IHTEN.KLYL VFEFLHQDLK
Os Cdc2   VPSTAIREIS LLKEMHHG.. ..NIVRLHDV IHSEK.RIYL VFEYLDLDLK
```

FIGURE 4A, 2

```
Pc Cdc2   KYMNSIP... .......... .....KDMML GAEMIKKFMS QLVSGVKYCH
Ca Cdc2   KYMESIP... .......... .....QGVGL GANMIKRFMN QLIRGIKHCH
Sc Cdc2   RYMEGIP... .......... .....KDQPL GADIVKKFMM QLCKGIAYCH
Ac Cdc2   KYMEALPVSE GGRGKALPDG STLDMNRLGL GEAMVKKFMA QLVEGIRYCH
En Cdc2   KYMEALPVSE GGRGRALPDG STLSRN.LGL GDAMVKKFMA QLIEGIRFCH
Sp Cdc2   KYMDRISETG AT........ ........SL DPRLVQKFTY QLVNGVNFCH
Rn Cdc2   KYLDSIPPGQ F......... .........M DSSLVKSYLY QILQGIVFCH
Hs Cdc2   KYLDSIPPGQ Y......... .........M DSSLVKSYLY QILQGIVFCH
Hs Cdk2   KFMDASALTG .......... .........I PLPLIKSYLF QLLQGLAFCH
Os Cdc2   KFMDSCPEFA .......... .........K NPTLIKSYLY QILRGVAYCH

Pc Cdc2   SHRILHRDLK PQNLLID.RE GNLKLADFGL ARAFGVPLRG YTHEVVTLWY
Ca Cdc2   SHRVLHRDLK PQNLLID.KE GNLKLADFGL ARAFGVPLRA YTHEVVTLWY
Sc Cdc2   SHRILHRDLK PQNLLIN.KD GNLKLGDFGL ARAFGVPLRA YTHEIVTLWY
Ac Cdc2   SHRVLHRDLK PQNLLID.RE GNLKLADFGL ARAFGVPLRT YTHEVVTLWY
En Cdc2   SHRVLHRDLK PQNLLID.RD GNLKLADFGL ARAFGVPLRT YTHEVVTLWY
Sp Cdc2   SRRIIHRDLK PQNLLID.KE GNLKLADFGL ARSFGVPLRN YTHEIVTLWY
Rn Cdc2   SRRVLHRDLK PQNLLIDDK. GTIKLADFGL ARAFGIPIRV YTHEVVTLWY
Hs Cdc2   SRRVLHRDLK PQNLLIDDK. GTIKLADFGL ARAFGIPIRV YTHEVVTLWY
Hs Cdk2   SHRVLHRDLK PQNLLIN.TE GAIKLADFGL ARAFGVPVRT YTHEVVTLWY
Os Cdc2   SHRVLHRDLK PQNLLIDRRT NALKLADFGL ARAFGIPVRT FTHEVVTLWY
```

FIGURE 4A, 3

```
Pc Cdc2   RAPEVLLGGR QYATALDIWS IGCIFAEMAT KKPLFPGDSE IDEIFRIFRI
Ca Cdc2   RAPEILLGGK QYSTGVDMWS VGCIFAEMCN RKPLFPGDSE IDEIFRIFRI
Sc Cdc2   RAPEVLLGGK QYSTGVDTWS IGCIFAEMCN RKPIFSGDSE IDQIFKIFRV
Ac Cdc2   RAPEILLGGR QYSTGVDMWS VGAIFAEMCT RKPLFPGDSE IDEIFKIFKL
En Cdc2   RSPEILLGGR QYSTGVDMWS CGAIFAEMCT RKPLFPGDSE IDEIFKIFRI
Sp Cdc2   RAPEVLLGSR HYSTGVDIWS VGCIFAEMIR RSPLFPGDSE IDEIFKIFQV
Rn Cdc2   RSPEVLLGSA RYSTPVDIWS IGTIFAELAT KKPLFHGDSE IDQLFRIFRA
Hs Cdc2   RSPEVLLGSA RYSTPVDIWS IGTIFAELAT KKPLFHGDSE IDQLFRIFRA
Hs Cdk2   RAPEILLGSK YYSTAVDIWS LGCIFAEMVT RRALFPGDSE IDQLFRIFRT
Os Cdc2   RAPEILLGSR QYSTPVDMWS VGCIFAEMVN QKPLFPGDSE IDELFKIFRV

Pc Cdc2   LGTPDENSWP GITSYPDFKA TFPKWSPKNL GELITELDSD GIDLLQKCLR
Ca Cdc2   LGTPNEEIWP DVNYLPDFKS SFPQWKKKPL SEAVPSLDAN GIDLLDQMLV
Sc Cdc2   LGTPNEAIWP DIVYLPDFKP SFPQWRRKDL SQVVPSLDPR GIDLLDKLLA
Ac Cdc2   LGTPDENTWP GVTSFPDFKA SFPKWKREDT RKLVPGLERN GLDLLDAMLE
En Cdc2   LGTPDETIWP GVTSFPDFKP TFPKWKREDI QNVVPGLEED GLDLLEALLE
Sp Cdc2   LGTPNEEVWP GVTLLQDYKS TFPRWKRMDL HKVVPNGEED AIELLSAMLV
Rn Cdc2   LGTPNNEVWP EVESLQDYKN TFPKWKPGSL ASHVKNLDEN GLDLLSKMLV
Hs Cdc2   LGTPNNEVWP EVESLQDYKN TFPKWKPGSL ASHVKNLDEN GLDLLSKMLI
Hs Cdk2   LGTPDEVVWP GVTSMPDYKP SFPKWARQDF SKVVPPLDED GRSLLSQMLH
Os Cdc2   LGTPNEQSWP GVSSLPDYKS AFPKWQAQDL ATIVPTLDPA GLDLLSKMLR
```

FIGURE 4A,4

```
Pc Cdc2  YYPAERISAK KALDHPYFDD FINLNRSNVV L......... ...
Ca Cdc2  YDPSRRISAK RALIHPYFND NDDRDHNNYN EDNIGIDKHQ NMQ
Sc Cdc2  YDPINRISAR RAAIHPYFQE S......... .......... ...
Ac Cdc2  YDPARRISAK QACMHPYFQA GSSAYSGRER LQPYP..... ...
En Cdc2  YDPARRISAK QACMHPYFQH GSSYYSGRAR RNGFH..... ...
Sp Cdc2  YDPAHRISAK RALQQNYLRD FH........ .......... ...
Rn Cdc2  YDPAKRISGK MALKHPYFDD LDNQIKKM.. .......... ...
Hs Cdc2  YDPAKRISGK MALNHPYFND LDNQIKKM.. .......... ...
Hs Cdk2  YDPNKRISAK AALAHPFFQD VTKPVPHLRL .......... ...
Os Cdc2  YEPNKRITAR QALEHEYFKD LEMVQ..... .......... ...
```

FIGURE 4B,1

```
cDNA      1   ATGGAGCAATATCAGAGGTTAGAGAAGATTGGAGAAGGaACTTATGGAGTTGTTTATAAa   60
          1   M  E  Q  Y  Q  R  L  E  K  I  G  E  G  T  Y  G  V  V  Y  K   20
Genomic   1   ATGGAGCAATATCAGAGGTTAGAGAAGATTGGAGAAGGgACTTATGGAGTTGTTTATAAg   60
          1   M  E  Q  Y  Q  R  L  E  K  I  G  E  G  T  Y  G  V  V  Y  K   20

cDNA     61   GCaAAGGATCTTGAAAGTGGtACAATTGTAGCTCTTAAgAAAATCCGaTTAGAaGCAGAA  120
         21   A  K  D  L  E  S  G  T  I  V  A  L  K  K  I  R  L  E  A  E   40
Genomic  61   GCcAAGGATCTTGAAAGTGGcACAATTGTAGCTCTTAAaAAAATCCGgTTAGAgGCAGAA  120
         21   A  K  D  L  E  S  G  T  I  V  A  L  K  K  I  R  L  E  A  E   40

cDNA    121   GATGAGGGAGTTCCTAGtACAGCAATTCGTGAgATATCaCTTTTGAAAGAgATGCACAAT  180
         41   D  E  G  V  P  S  T  A  I  R  E  I  S  L  L  K  E  M  H  N   60
Genomic 121   GATGAGGGAGTTCCTAGcACAGCAATTCGTGAaATATCtCTTTTGAAAGAaATGCACAAT  180
         41   D  E  G  V  P  S  T  A  I  R  E  I  S  L  L  K  E  M  H  N   60

cDNA    181   GATAATGTtGTAAGACTTTTGAATATaATTCATCAaGAgTCACGTtTATATCTTGTTTTT  240
         61   D  N  V  V  R  L  L  N  I  I  H  Q  E  S  R  L  Y  L  V  F   80
Genomic 181   GATAATGTcGTAAGACTTTTGAATATtATTCATCAgGAaTCACGTcTATATCTTGTTTTT  240
         61   D  N  V  V  R  L  L  N  I  I  H  Q  E  S  R  L  Y  L  V  F   80

cDNA    241   GAATTTCTTGATCTTGATTTaAAAAAgTATATGAATAGTATTCCAAAgGACATGATGCTT  300
         81   E  F  L  D  L  D  L  K  K  Y  M  N  S  I  P  K  D  M  M  L  100
Genomic 241   GAATTTCTTGATCTTGATTTgAAAAAaTATATGAATAGTATTCCAAAaGACATGATGCTT  300
         81   E  F  L  D  L  D  L  K  K  Y  M  N  S  I  P  K  D  M  M  L  100
```

FIGURE 4B,2

```
cDNA     301  GGtGCaGAAATGATtAAAAAgTTTATGTCaCAACTTGTATCAGGTGTTAAATATTGTCAT  360
         101  G  A  E  M  I  K  K  F  M  S  Q  L  V  S  G  V  K  Y  C  H   120
Genomic  301  GGaGCtGAAATGATcAAAAAaTTTATGTCtCAACTTGTATCAGGTGTTAAATATTGTCAT  360
         101  G  A  E  M  I  K  K  F  M  S  Q  L  V  S  G  V  K  Y  C  H   120

cDNA     361  TCTCATCGTATTCTTCATCGTGACTTGAAaCCaCAAAATCTTCTTATaGATCGAGAAGGA  420
         121  S  H  R  I  L  H  R  D  L  K  P  Q  N  L  L  I  D  R  E  G   140
Genomic  361  TCTCATCGTATTCTTCATCGTGACTTGAAgCCcCAAAATCTTCTTATtGATCGAGAAGGA  420
         121  S  H  R  I  L  H  R  D  L  K  P  Q  N  L  L  I  D  R  E  G   140

cDNA     421  AATCTTAAAtTaGCaGATTTtGGGCTTGCaaGGGCgTTTGGTGTTCCaTTgCGTGGTTAT  480
         141  N  L  K  L  A  D  F  G  L  A  R  A  F  G  V  P  L  R  G  Y   160
Genomic  421  AATCTTAAAcTtGCtGATTTcGGGCTTGCtcGGGCaTTTGGTGTTCCtTTaCGTGGTTAT  480
         141  N  L  K  L  A  D  F  G  L  A  R  A  F  G  V  P  L  R  G  Y   160

cDNA     481  ACTCATGAaGTTGTTACACTTTGGTATCGTGCTCCAGAAGTTCTTTTAGGTGGTCGACAA  540
         161  T  H  E  V  V  T  L  W  Y  R  A  P  E  V  L  L  G  G  R  Q   180
Genomic  481  ACTCATGAgGTTGTTACACTTTGGTATCGTGCTCCAGAAGTTCTTTTAGGTGGTCGACAA  540
         161  T  H  E  V  V  T  L  W  Y  R  A  P  E  V  L  L  G  G  R  Q   180

cDNA     541  TATGCAACAGCgCTTGATATaTGGAGCATTGGATGTATTTTTGCaGAAATGGCTACAAAA  600
         181  Y  A  T  A  L  D  I  W  S  I  G  C  I  F  A  E  M  A  T  K   200
Genomic  541  TATGCAACAGCaCTTGATATtTGGAGCATTGGATGTATTTTTGCtGAAATGGCTACAAAA  600
         181  Y  A  T  A  L  D  I  W  S  I  G  C  I  F  A  E  M  A  T  K   200

cDNA     601  AAgCCaTTATTTCCAGGtGATTCTGAAATTGATGAAATATTtAGAATATTTAGAATATTA  660
         201  K  P  L  F  P  G  D  S  E  I  D  E  I  F  R  I  F  R  I  L   220
Genomic  601  AAaCCgTTATTTCCAGGcGATTCTGAAATTGATGAAATATTcAGAATATTTAGAATATTA  660
         201  K  P  L  F  P  G  D  S  E  I  D  E  I  F  R  I  F  R  I  L   220
```

FIGURE 4B,3

```
cDNA     661  GGgACtCCaGATGAAAATTCTTGGCCTGGTATTACATCtTATCCgGATTTTAAgGCAACT  720
         221  G  T  P  D  E  N  S  W  P  G  I  T  S  Y  P  D  F  K  A  T   240
Genomic  661  GGaACaCCtGATGAAAATTCTTGGCCTGGTATTACATCaTATCCtGATTTTAAaGCAACT  720
         221  G  T  P  D  E  N  S  W  P  G  I  T  S  Y  P  D  F  K  A  T   240

cDNA     721  TTTCCaAAATGGTCACCAAAAAATCTTGGAGAATTAATTACAGAACTTGATAGTGATGGA  780
         241  F  P  K  W  S  P  K  N  L  G  E  L  I  T  E  L  D  S  D  G   260
Genomic  721  TTTCCaAAATGGTCACCAAAAAATCTTGGAGAATTAATTACAGAACTTGATAGTGATGGA  780
         241  F  P  K  W  S  P  K  N  L  G  E  L  I  T  E  L  D  S  D  G   260

cDNA     781  ATAGATTTATTACAGAAATGTCTtAGATATTATCCTGCTGAACGTATTAGcGCtAAAAAa  840
         261  I  D  L  L  Q  K  C  L  R  Y  Y  P  A  E  R  I  S  A  K  K   280
Genomic  781  ATAGATTTATTACAGAAATGTCTcAGATATTATCCTGCTGAACGTATTAGtGCaAAAAAg  840
         261  I  D  L  L  Q  K  C  L  R  Y  Y  P  A  E  R  I  S  A  K  K   280

cDNA     841  GCTCTCGATCATCCtTATTTTGATGATTTCATTAATaTCAATAGATCTAATGTGGTGCTA  900
         281  A  L  D  H  P  Y  F  D  D  F  I  N  L  N  R  S  N  V  V  L   300
Genomic  781  GCTCTCGATCATCCaTATTTTGATGATTTCATTAATcTCAATAGATCTAATGTGGTGCTA  900
         281  A  L  D  H  P  Y  F  D  D  F  I  N  I  N  R  S  N  V  V  L   300

cDNA     903  TAG  903
         301  *    301
Genomic  903  TAG  903
         301  *    301
```

METHOD FOR IDENTIFYING INHIBITORS OF CDC2 PROTEIN KINASE FROM *PNEUMOCYSTIS CARINII*

STATEMENT AS TO FEDERALLY SPONSORED RESEARCH

Funding for the work described herein was provided by the federal government, which has certain rights in the invention.

BACKGROUND OF THE INVENTION

This invention relates to the identification of a cell cycle control molecule in *Pneumocystis carinii.*

*Pneumocystis carinii* (*P. carinii*) causes severe pneumonia in patients with chronic immunosuppression. Although *P. carinii* pneumonia is most frequently associated with acquired immune deficiency syndrome (AIDS), patients with solid tumors, hematological malignancies, organ transplantation, and inflammatory conditions requiring prolonged immunosuppression with corticosteroids or cytotoxic agents are also at increased risk for developing *P. carinii* pneumonia. The mortality of *P. carinii* pneumonia remains an unacceptable 15% to 40%, being substantially higher in immunosuppressed patients without AIDS. In addition, medications currently used for preventing and treating *P. carinii* pneumonia are associated with significant side effects in many patients, limiting their use. Therefore, development of newer classes of therapeutic agents for this infection remains a pressing concern.

*P. carinii* has been shown to be of fungal origin on the basis of ribosomal RNA gene homology and enzyme biochemistry studies. Phylogenetically, *P. carinii* is most closely related to the fission yeast *Schizosaccharomyces pombe*, and to the Ustomycetous red yeast fungus. A complete understanding of the life cycle of *P. carinii* is currently lacking, confounding the ability to culture this organism. Ultrastructural studies indicate that *P. carinii* has a unique life cycle consisting of both diminutive trophozoites about 1–2 microns in size and larger cystic forms about 8 microns in size. The interaction of trophozoites with alveolar epithelial cells is an integral component of the organism's life cycle and modulates cellular proliferation. Despite numerous efforts employing a variety of cell lines, media, and methodologies, the in vitro cultivation of *P. carinii* has met with rather limited success and no system yet exists to maintain *P. carinii* continuously in a cell free system. The limited availability of short term culture and inability to propagate *P. carinii* has rendered basic studies of this organism difficult, hampering development of new therapies.

SUMMARY OF THE INVENTION

The invention is based on the discovery of a key protein that aids in the regulation of the cell cycle in *Pneumocystis carinii*. Cloning and sequencing of the complete cdc2 gene identified the unique carboxyl-terminus of the *P. carinii* Cdc2 polypeptide. Antibodies generated against this carboxyl-terminus region have specific binding affinity for *P. carinii* Cdc2 polypeptide and are beneficial in diagnosing and monitoring *P. carinii* infection in patients. Expression of *P. carinii* Cdc2 polypeptide in cdc2-mutant yeast and other cdc2-mutant organisms provides a useful model for studying the life cycle of *P. carinii* and for identifying novel therapeutics.

In general, the invention features an isolated polynucleotide encoding a *Pneumocystis carinii* Cdc2 polypeptide having the amino acid sequence set out in FIG. 3 and FIG. 4 (SEQ ID NO:1 and SEQ ID NO:10), and biologically active polypeptide fragments thereof. The polynucleotide can include a nucleic acid sequence selected from the group consisting of:

a) genomic nucleic acid sequence (SEQ ID NO:1);

b) cDNA nucleic acid sequence (SEQ ID NO:9);

c) an RNA analog of a);

d) an RNA analog of b);

e) a polynucleotide having a nucleic acid sequence complementary to a), b), c), or d); and f) a nucleic acid fragment of a), b), c), d), or e) that is at least 15 nucleotides in length and that hybridizes under stringent conditions to DNA encoding the polypeptide of *P. carinii* Cdc2.

In another embodiment, the invention features an *S. pombe* expression vector comprising a DNA molecule encoding a *Pneumocystis carinii* Cdc2 polypeptide having the amino acid sequence set out in FIG. 3 and FIG. 4 (SEQ ID NO:1 and SEQ ID NO:10), or biologically active polypeptide fragments thereof.

The invention also features a transformed host comprising an exogenous DNA molecule encoding *P. carinii* Cdc2 polypeptide or a biologically active fragment thereof. The transformed host can be, for example, *Schizosaccharomyces pombe* or *Saccharomyces cerevisiae.*

In another embodiment, the invention features an isolated polypeptide comprising the amino acid sequence Phe-Ile-Asn-Leu-Asn-Arg-Ser-Asn-Val-Val-Leu (SEQ ID NO:11). Antibodies having specific binding affinity for a polypeptide comprising the amino acid sequence Phe-Ile-Asn-Leu-Asn-Arg-Ser-Asn-Val-Val-Leu (SEQ ID NO:11) are also included within the invention.

In still another embodiment, the invention features a method for diagnosing or monitoring *P. carinii* infection in a patient, comprising detecting a Cdc2 polypeptide from *P. carinii* in a tissue or fluid sample from the patient. Detection can be through use of an antibody having specific binding affinity for a polypeptide comprising the amino acid sequence Phe-Ile-Asn-Leu-Asn-Arg-Ser-Asn-Val-Val-Leu (SEQ ID NO:11). Likewise, *P. carinii* infection in a patient can be diagnosed or monitored by detecting the presence or amount of a cdc2 nucleic acid from *P. carinii* in a tissue or fluid sample from said patient, for example through use of polymerase chain reaction.

The invention also features a method for identifying potential inhibitors of *P. carinii* cdc2 gene expression or protein activity, comprising:

a) growing a conditional-lethal mutant host cell culture under non-permissive conditions in the presence of a candidate agent, wherein the conditional-lethal mutant host cell culture is capable of expressing *P. carinii* Cdc2 polypeptide under the non-permissive conditions, thereby permitting growth of the conditional-lethal mutant host cell culture under non-permissive conditions; and b) monitoring the ability of the conditional-lethal mutant host cell culture to grow under non-permissive conditions in the presence of the candidate agent, and identifying the candidate agent as a potential inhibitor if the growth is inhibited relative to a control culture. The conditional-lethal mutant host cell culture can be, for example, a conditional-lethal mutant of *Schizosaccharomyces pombe.*

In another embodiment, the invention features a method for identifying an agent inhibiting the phosphorylation activity of *P. carinii* cdc2 polypeptide, comprising incubating an isolated Cdc2 polypeptide, for example a recombinant Cdc2 polypeptide, and a substrate of Cdc2 polypeptide with the agent to determine if phosphorylation of the substrate is inhibited. The substrate can be, for example, H1 histone, Cdc25 polypeptide, nuclear lamins, retinoblastoma protein, cyclin B, or DNA polymerase alpha.

"Polypeptide" refers to any chain of amino acids, regardless of length or post-translational modification (e.g., glycosylation or phosphorylation).

"Biologically active polypeptide fragments" refers to a fragment of a complete polypeptide that retains an activity characteristic of the complete polypeptide, although regulation of the activity may be altered.

"Transformed host" refers to a cell into which (or into an ancestor of which) a DNA molecule has been introduced by means of recombinant DNA techniques.

"High stringency conditions" refers to hybridization conditions used to identify nucleic acids that have a high degree of homology to the probe. High stringency conditions can include the use of low ionic strength and high temperature for washing, for example, 0.015M NaCl/0.0015M sodium citrate (0.1× SSC); 0.1% sodium dodecyl sulfate (SDS) at 65° C. Alternatively, a denaturing agent such as formamide can be employed during hybridization, e.g. 50% formamide with 0.1% bovine serum albumin/0/1% Ficoll/0.1% polyvinylpyrrolidone/50 mM sodium phosphate buffer at pH 6.5 with 750 mM NaCl, 75 mM sodium citrate at 42° C. Another example is the use of 50% formamide, 5× SSC (0.75M NaCl, 0.075M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2× SSC and 0.1% SDS.

"Moderate stringency conditions" refers to hybridization conditions used to identify nucleic acids that have less homology to the probe than nucleic acids identified under high stringency conditions. Moderate stringency conditions can include the use of higher ionic strength and/or lower temperatures for washing of the hybridization membrane, compared to the ionic strength and temperatures used for high stringency hybridization. For example, a wash solution comprising 0.060M NaCl/0.0060M sodium citrate (4× SSC) and 0.1% SDS can be used at 50° C., with a last wash in 1× SSC at 65° C. Alternatively, a hybridization wash in 1× SSC at 37° C. can be used.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the appended claims.

BRIEF DESCRIPTION OF THE FIGURES

FIG. 3A is the nucleotide and predicted amino-acid sequence of *P. carinii* cdc2. Shown in upper-case are seven exons determined by comparison of the genomic and cDNA clones. The intron 5' donor and 3' acceptor splice sites are underlined.

FIG. 4A is a comparison of the predicted *P. carinii* Cdc2 amino-acid sequence (SEQ ID NO:10) to other eukaryotic Cdc2 proteins. Amino-acid alignments are as follows: Pc, *P. carinii*; Ca, *Candida albicans* (SEQ ID NO:18); Sc, *Saccharomyces cerevisiae* (SEQ ID NO:19); Ac, *Ajellomyces capsulata* (SEQ ID NO:20); En, *Emericella nidulans* (SEQ ID NO:21); Sp, *Schizosaccharomyces pombe* (SEQ ID NO:22); Rn, *Rattus norvegicus* (SEQ ID NO:23); Hs, *Homo sapiens* (SEQ ID NO:24 and SEQ ID NO:25); Os, *Oryza sativa* (SEQ ID NO:26). Bold type indicates the conserved ATP-binding and PSTAIRE sites from which the degenerate PCR primers were derived. Periods are used to maximize alignment.

FIG. 4B is a comparison of predicted *P. carinii* Cdc2 amino acid sequences from the genomic and cDNA clone. The *P. carinii* cdc2 cDNA was compared to the genomic cdc2 sequence following deletion of the introns to maximize alignment. Lower case bold characters represent mucleotide mismatches. The upper case bold L represents a leucine residue from the genomic clone which corresponds to an isoleucine in *P. carinii* cd2 cDNA.

DETAILED DESCRIPTION

Figure 1:
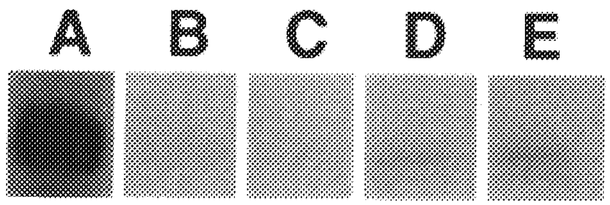
FIG. 1 is an autoradiogram depicting kinase activity of the *P. carinii* Cdc2 polypeptide. Shown is H1 histone phosphorylated with immunoprecipated *P. carinii* Cdc2-like protein in the presence of [$^{32}$P]-τ-ATP. Lane A. *P. carinii* lysate immunoprecipitated with anti-PSTAIR antibody and submitted to histone kinase assay. Lane B. *P. carinii* lysate reacted with non-immune rabbit IgG. Lane C. Preincubation of anti-PSTAIR with cognate peptide. Lane D. Immunoprecipitation of lysate from an equal volume of uninfected rat lung using anti-PSTAIR. Lane E. Uninfected rat lung lysate reacted with non-immune rabbit IgG.

*P. carinii* is a pathogenic fungus that causes severe pneumonia in chronically immunosuppressed patients. Little information is known about the organism's life cycle, preventing its in vitro culturing. The present inventors have identified a key protein in *P. carinii* that is important in controlling the cell cycle in most eukaryotes.

The orderly progression of the eukaryotic cell cycle is precisely regulated by a number of cell division cycle (cdc) control proteins. Much of what has been learned of eukaryotic cell cycle control in species as diverse as fungi and higher eukaryotes, has been learned by studying cdc mutants of yeast, particularly *S. pombe*, an easily culturable organism. Studies of cdc mutants have lead to identification of a number of critical growth regulatory genes in fungi. Of particular importance is the cdc2 gene, the product of which has been termed Cdc2 or $p34^{cdc2}$, a serine-threonine protein kinase required for traverse from the G2 phase to the M phase of the cell cycle, and for entry into S phase from the G1 phase at a point known as START in yeast.

The level of expression of Cdc2 protein is generally constitutive throughout most eukaryotic cell cycles, with the relative kinase activity of Cdc2 being controlled over the cell cycle through a number of positive and negative acting signals. Activation of *S. pombe* Cdc2 kinase requires association with a regulatory cyclin molecule, as well as both the removal of negative acting phosphorylations (e.g. tyr 15) and addition of positive acting phosphorylations (e.g. thr 161/167).

An isolated polynucleotide of the invention encodes a *P. carinii* Cdc2 polypeptide having the amino acid sequence shown in FIGS. 3 and 4 (SEQ ID NO:1 and SEQ ID NO:10), or biologically active polypeptide fragments. Biologically active polypeptide fragments of the *P. carinii* Cdc2 polypeptide refers to fragments of the polypeptide that retain kinase ability and are able to phosphorylate proteins such as histone H1, even though regions of the full-length polypeptide have been removed. For example, a biologically active fragment of Cdc2 may retain only the kinase domains and not the carboxyl terminus, since the carboxyl terminus is generally not associated with enzymatic activity.

A polynucleotide of the invention may be in the form of RNA or in the form of DNA, including cDNA, synthetic DNA or genomic DNA. The DNA may be double-stranded or single-stranded, and if single-stranded, can be either the coding strand or non-coding strand. An RNA analog may be, for example, mRNA or a combination of ribo- and deoxyribonucleotides. Illustrative examples of a polynucleotide of the invention are shown in FIGS. 3 and 4 (SEQ ID NO:1 and SEQ ID NO:9).

A polynucleotide of the invention typically is at least 15 nucleotides (or base pairs, bp) in length. In some embodiments, a polynucleotide is about 20 to 100 nucleotides in length, or about 100 to 500 nucleotides in length. In other embodiments, a polynucleotide is greater than about 1000 nucleotides in length and encodes a polypeptide having the amino acid sequence shown in FIG. 4 (SEQ ID NO:1 and SEQ ID NO:10).

In some embodiments, a polynucleotide of the invention encodes analogs or derivatives of a polypeptide having part or all of the deduced amino acid sequence of the Cdc2 polypeptide shown in FIGS. 3 and 4 (SEQ ID NO:1 and SEQ ID NO:10). Such fragments, analogs or derivatives include, for example, naturally occurring allelic variants, non-naturally occurring allelic variants, deletion variants and insertion variants, that do not substantially alter the function of the polypeptide. The nucleotide sequence may be identical to the nucleotide sequence shown in FIGS. 3 and 4 (SEQ ID NO:1 and SEQ ID NO:9) or may be a different nucleotide sequence that, due to the degeneracy of the genetic code, encodes the same amino acid sequence as the Cdc2 polypeptide.

It should be appreciated that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties. For example, isoleucine and valine are similar amino acids. Similarity between amino acid pairs has been assessed in the art in a number of ways. For example, Dayhhoff et al. (1978) in *Atlas of Protein Sequencing and Structure*, Vol. 5, Suppl. 3, pp. 345–352, which is incorporated by reference herein, provides frequency tables for amino acid substitutions which can be employed as a measure of amino acid similarity. The frequency tables of Dayhoff et al. are based on comparisons of amino acid sequences for proteins having the same function from a variety of evolutionarily different sources.

An isolated polynucleotide of the invention may hybridize under stringent conditions with a nucleic acid encoding the polypeptide described in FIGS. 3 and 4 (SEQ ID NO:1 and SEQ ID NO:10). The isolated polynucleotides may be useful as nucleic acid probes for identifying *P. carinii* cdc2 nucleic acid sequences under high stringency conditions and for cdc2 nucleic acid sequences from other pathogenic fungal species such as Histoplasma, Candida and Aspergillus under more moderate stringency. It is generally preferred that a probe of at least about 20 nucleotides in length be used, preferably at least about 50 nucleotides, more preferably at least about 100 nucleotides.

Hybridization typically involves Southern analysis (Southern blotting), a method by which the presence of DNA sequences in a target nucleic acid mixture are identified by hybridization to a labeled oligonucleotide or DNA fragment probe. Southern analysis typically involves electrophoretic separation of DNA digests on agarose gels, denaturation of the DNA after electrophoretic separation, and transfer of the DNA to a suitable membrane support, such as nitrocellulose or nylon, for analysis with a labeled probe.

Labels for hybridization probes can include, but are not limited to, radioactive groups, fluorescent groups, and ligands such as biotin to which specific binding partners (which are in turn labeled) bind. It is the label that allows detection of the hybridization probe to the target nucleic acid.

A polynucleotide can hybridize under high stringency conditions to a *P. carinii* cdc2 polynucleotide disclosed herein. High stringency conditions are used to identify nucleic acids that have a high degree of homology to the probe. High stringency conditions can include the use of low ionic strength and high temperature for washing, for example, 0.015M NaCl/0.0015M sodium citrate (0.1× SSC); 0.1% sodium dodecyl sulfate (SDS) at 65° C. Alternatively, a denaturing agent such as formamide can be employed during hybridization, e.g. 50% formamide with 0.1% bovine serum albumin/0/1% Ficoll/0.1% polyvinylpyrrolidone/50 mM sodium phosphate buffer at pH 6.5 with 750 mM NaCl, 75 mM sodium citrate at 42° C. Another example is the use of 50% formamide, 5× SSC (0.75M NaCl, 0.075M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2× SSC and 0.1% SDS.

Moderate stringency conditions refers to hybridization conditions used to identify nucleic acids that have less homology to the probe than nucleic acids identified under high stringency conditions. Moderate stringency conditions can include the use of higher ionic strength and/or lower temperatures for washing of the hybridization membrane, compared to the ionic strength and temperatures used for high stringency hybridization. For example, a wash solution comprising 0.060M NaCl/0.0060M sodium citrate (4× SSC) and 0.1% SDS can be used at 50° C., with a last wash in 1× SSC at 65° C. Alternatively, a hybridization wash in 1× SSC at 37° C. can be used.

Hybridization can also be done by Northern analysis (Northern blotting), a method used to identify RNAs that hybridize to a known probe such as an oligonculeotide, DNA fragment, cDNA or fragment thereof, or RNA fragment. The RNA to be analyzed can be usually electrophoretically separated on an agarose or polyacrylamide gel, transferred to nitrocellulose, nylon, or other suitable membrane, and hybridized with the probe, using standard techniques such as those described in sections 7.39–7.52 of Sambrook et al., (1989) *Molecular Cloning*, second edition, Cold Spring Harbor Laboratory, Plainview, N.Y.

In addition, the isolated DNA molecules may be used in association with regulatory DNA molecules in a recombinant expression vector to produce recombinant *P. carinii* Cdc2 polypeptide. Regulatory DNA molecules encode proteins that control the expression of polypeptides or may contain recognition, promotor and secretion sequences. See, e.g., U.S. Pat. No. 5,269,193 incorporated herein by reference. Techniques in recombinant protein production and purification are readily accessible in the art. See, for example, Sambrook et al., (1989) *Molecular Cloning*, second edition, Cold Spring Harbor Laboratory, Plainview, N.Y.

For example, expression vectors can be employed to allow production of *P. carinii* Cdc2 polypeptide in *S. pombe*. Such an expression vector can include, by way of illustration, a polynucleotide encoding a *P. carinii* Cdc2 polypeptide that has the amino acid sequence shown in FIGS. 3 and 4 (SEQ ID NO:1 and SEQ ID NO:10), or biologically active polypeptides thereof, in association with a polynucleotide, including an inducible promoter, that permits growth on media lacking leucine.

In another aspect of the invention, a transformed host is described. The transformed host includes an exogenous polynucleotide encoding *P. carinii* Cdc2 polypeptide or a biologically active fragment thereof. Nonlimiting examples of potential hosts include mammalian cell lines, bacterial cells such as *E. coli*, insect cells, and yeast. Preferred hosts include the yeasts *S. pombe* and *S. cerevisiae. S. pombe*, a fission yeast, and *S. cerevisiae*, a budding yeast, are excellent model systems to study the biological role of Cdc2 polypeptide in regulating the cell cycle as well as to screen for *P. carinii* Cdc2 kinase inhibitors. Both organisms have a haploid phase that facilitates genetic analysis. Conditional-lethal cdc2 mutants have been identified in each organism. Such mutants fail to survive or fail to grow at non-permissive growth conditions. For example, the conditional-lethal mutant may be temperature-sensitive, i.e. the mutant will function normally at permissive temperatures, but fails to function at non-permissive temperatures.

The invention also includes an isolated polypeptide having the amino acid sequence from about amino acid 290 to about amino acid 300 (SEQ ID NO:11), as set out in FIG. 4. This amino acid sequence is unique to the *P. carinii* Cdc2 polypeptide. Given this amino acid sequence, antibodies with specificity for an epitope defined by this amino acid sequence may be prepared by immunizing a suitable animal such as a rabbit. Polyclonal and monoclonal antibody production and purification techniques are standard in the art.

Another feature of the invention is a method for diagnosing or monitoring *P. carinii* infection in a patient. It includes removing a tissue or fluid sample from a patient and detecting the presence or amount of *P. carinii* in the sample. Sputum or respiratory secretions often contain infecting organisms during infection and may be easily obtained from a patient and used as samples. Detecting the presence or amount of *P. carinii* in a sample may include detecting Cdc2 polypeptide. A preferred method of detecting Cdc2 polypeptide includes using an antibody with specificity for the amino acid sequence from about amino acid 290 to about amino acid 300 as described in FIG. 4 (SEQ ID NO:11). For example, the antibody may be attached to a solid phase and exposed to a sample from a patient. Bound Cdc2 may be detected through a labeled second antibody with specificity for a different epitope, such as the conserved proline-serine-threonine-alanine-isoleucine-arginine (PSTAIR) motif found in Cdc2 proteins of related fungi. Alternatively, proteins may be extracted from the sample and separated by SDS polyacrylamide gel electrophoresis. After transfer to a membrane, Cdc2 may be detected with a labeled antibody with specificity for the amino acid seqeuence from amino acid 290 to about amino acid 300 as described in FIG. 4 (SEQ ID NO:11).

Antibodies may be enzymatically labeled, or may be labeled with a radioactive group or fluorescent group. For instance, antibody may be labeled with an enzyme that reacts with a colorless substrate to generate a colored reaction product. Nonlimiting examples of such enzymes include alkaline phosphatase, horseradish peroxidase, and p-nitrophenyl phosphatase. The label may be on the antibody with specificity for the amino acid sequence from about amino acid 290 to about amino acid 300 as set out in FIG. 4 (SEQ ID NO:11), or may be on a second antibody with specificity for either a different Cdc2 epitope or for the antibody itself, e.g., rabbit anti-mouse Ig antibody.

In another aspect, cdc2 nucleic acid may be detected in the samples by using the nucleic acid sequences described in FIGS. 3 and 4 (SEQ ID NO:1 and SEQ ID NO:9) or fragments thereof as probes. It is generally preferred that a probe of at least about 20 nucleotides in length be used, preferably at least about 50 nucleotides, more preferably at least about 100 nucleotides. The probe may be hybridized to nucleic acids in the sample, using methods described, for example, in Sambrook et al., (1989) *Molecular Cloning*, second edition, Cold Spring Harbor Laboratory, Plainview, N.Y.

Alternatively, nucleic acid amplification technology such as polymerase chain reaction (PCR) may be used to detect *P. carinii* nucleic acid sequences, using oligonucleotides corresponding to portions of the polynucleotide sequences shown in FIGS. 3 and 4 (SEQ ID NO:1 and SEQ ID NO:9). Amplification techniques are described in U.S. Pat. No. 4,683,195, incorporated herein by reference, and subsequent modifications of the procedure described therein. Generally, sequence information from the ends of the region of interest or beyond is employed to design oligonucleotide primers that are identical or similar in sequence to opposite strands of the template to be amplified. PCR can be used to amplify specific RNA sequences, specific DNA sequences from total genomic DNA, cDNA transcribed from cellular RNA, bacteriophage or plasmid sequences, and the like.

In an additional embodiment, a method for identifying an inhibitor of *P. carinii* cdc2 gene expression or Cdc2 polypeptide activity is described. In this method, a host culture of an organism carrying a conditional-lethal cdc2 mutation may be grown at the non-permissive condition in the presence of a candidate agent. An agent may be a chemical compound, a mixture of chemical compounds, or a biological macromolecule such as an anti-sense nucleic acid. The conditional-lethal mutant is capable of expressing *P. carinii* Cdc2 polypeptide at the non-permissive condition, allowing growth of the conditional-lethal mutant host culture under these (otherwise non-permissive) conditions. The ability of the conditional-lethal mutant host cell culture to grow under non-permissive conditions is monitored. A return to an inability to grow at the non-permissive condition may indicate that *P. carinii* cdc2 gene expression or Cdc2 polypeptide activity has been inhibited. A preferred host is a temperature-sensitive cdc2 mutant of *S. pombe*.

*P. carinii* Cdc2 kinase inhibitors may also be screened in vitro by monitoring the phosphorylation of its substrates using standard techniques. For example, isolated Cdc2 polypeptide may be incubated with an isolated polypeptide substrate in a suitable kinase buffer that includes labeled ATP and a candidate agent. Isolated Cdc2 polypeptide may be recombinant in nature. Various substrates having relevance to all phases of the cell cycle may be used, including without limitation H1 histone, Cdc25 polypeptide, nuclear lamins, retinoblastoma protein (pRb), cyclin B and DNA polymerase alpha. A preferred substrate of Cdc2 polypeptide is H1 histone. Phosphorylated substrate is detected by measuring the amount of labeled phosphate that becomes incorporated into substrate. Alternatively, the polypeptides can be separated by SDS polyacrylamide gel-electrophoresis and transferred to a membrane. An autoradiogram then allows detection of the phosphorylation state of the substrate.

The invention will be further described in the following examples, which do not limit the scope of the invention described in the claims.

EXAMPLES

An antibody to a conserved fungal Cdc2 protein motif was used to identify a Cdc2 protein from *P. carinii* extracts. The Cdc2 protein was functionally shown to be a kinase, with higher activity in *P. carinii* trophozoites compared to cysts. Oligonucleotide primers to conserved fungal Cdc2 protein motifs were designed and used to amplify a fragment from *P. carinii* genomic DNA. Subsequently, the complete genomic and cDNA sequences of the *P. carinii* cdc2 gene were cloned and sequenced. Expression of *P. carinii* Cdc2 protein in temperature sensitive cdc2-mutant *S. pombe* restored proliferation.

Example 1

Preparation of *Pneumocystis carinii*

*P. carinii* cannot be routinely propagated in-vitro and instead are isolated from the lungs of infected rats.

Specific pathogen free Harlan Sprague-Dawley rats were freely provided with drinking water containing dexamethasone (2 mg/liter), tetracycline (500 mg/liter) and nystatin (200,000 U/liter) and fed an 8% protein diet in order to intensify the severity of infection. On a weekly basis, the animals also received oral ciprofloxacin (0.45 g/liter) for two consecutive days to reduce the risk of bacterial infections. After five days of immunosuppression, rats were transtracheally inoculated with approximately 500,000 *P. carinii* cysts prepared by homogenizing infected rat lung in a Stomacher microbiological blender. After tracheal injection, the rats were immunosuppressed for an additional 6–8 weeks and sacrificed. *P. carinii* were purified by homogenation and differential filtration through 10 micron filters that retain lung cells but allow passage of *P. carinii*. The filtrates were collected and centrifuged at about 1500×g for 30 minutes. Each pellet was resuspended in 5 ml of HBSS. *P. carinii* were quantified by spotting duplicate 10 μl aliquots of suspension onto slides and staining with modified Wright-Giemsa (Diff Quick). The material was discarded if other microorganisms were detected.

Example 2

Kinase Activity of the Cdc2-like molecule from *P. carinii* A Cdc2-like protein was identified in *P. carinii* by immunoprecipitation with a polyclonal antibody generated against the conserved proline-serine-threonine-alanine-isoleucine-arginine (PSTAIR) motif found in Cdc2 proteins of related fungi. The kinase activity of the Cdc2-like protein was assessed by the ability of immunoprecipitates to phosphorylate histone H1, an activity characteristic of Cdc2 proteins.

Extracts of *P. carinii* were prepared by first suspending about $5\times10^8$ *P. carinii* in 250 mM NaCl, 50 mM Tris-HCl pH 7.4, 0.1% Triton X-100, 5 mM EDTA, 5 mM NaVanadate, 5 mM NaF, 50 μg/ml PMSF, 1 μg/ml leupeptin and 0.1 TIU aprotinin lysis buffer. After sonicating to disrupt cell walls, soluble proteins were recovered by centrifuging at approximately 12,000×g for 10 minutes. Protein concentrations were measured by the BCA method (Pierce Chemical Company, Rockford, Ill.).

Identical aliquots of protein extract were preabsorbed with 50% protein A-Sepharose (Sigma Chemical Co., St. Louis, Mo.) and centrifuged at approximately 12,000×g for 10 minutes. The supernatant was incubated with 50 μg/ml of either anti-PSTAIR antibody (Upstate Biotechnologies Inc., Lake Placid, N.Y.) or non-immune rabbit IgG (Sigma Chemical Co., St. Louis, Mo.) for at least 60 minutes at 4° C. A control immunoprecipitation with anti-PSTAIR antibody pretreated with its cognate peptide for one hour was also performed. Protein-antibody complexes were precipitated with 50% protein A-Sepharose by centrifugation at approximately 12,000×g for 10 minutes. After washing the pellets twice in lysis buffer and twice in 50 mM Tris HCl pH 7.4, 10 mM $MgCl_2$ and 1 mM DTT kinase buffer, the pellets were resuspended in kinase buffer containing 5 μM ATP, 100 μg/ml histone H1 and 0.1 μCi/μl $^{32}$P-γ-ATP (New England Nuclear, Boston, Mass.) and incubated for 10 minutes at 30° C. Kinase reactions were stopped by addition of Laemmli buffer with 5% 2-mercaptoethanol, resolved by 12% SDS-PAGE and exposed to autoradiography film (see FIG. 1, lanes A–C).

Kinase activity was consistently detected in *P. carinii*-infected lung extracts immunoprecipitated with anti-PSTAIR antibody, but not non-immune rabbit IgG. Preincubation of anti-PSTAIR antibody with cognate peptide completely inhibited precipitation of protein kinase activity.

Additional immunoprecipitations and kinase assays were performed with extracts from uninfected rats, housed separately from *P. carinii*-infected rats (see FIG. 1, lanes D and E). Uninfected rat lung processed in an identical manner failed to demonstrate any residual protein kinase activity after immunoprecipitation with anti-PSTAIR, thus demonstrating that the Cdc2-like kinase activity was specifically derived from *P. carinii* and not the result of rat lung contamination.

Example 3

Determination of the activity of the *P. carinii* Cdc2-like protein kinase in cysts and trophozoites The activity of the Cdc2-like protein was assayed in isolated populations of *P. carinii* cysts and trophozoites to determine if it was differentially regulated during the life cycle of the organism.

Rat lungs were infected with *P. carinii* as described in Example 1 and homogenates made. Cysts and trophozoites were separated by differential filtration. *P. carinii* cysts were retained by a 3 micron nucleopore filter, whereas trophozoites passed through and were collected by centrifugation. This method yields populations with greater than 99% trophozoites and greater than forty-fold enrichment of *P. carinii* cysts.

Figure 2:
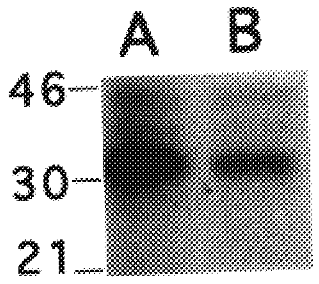
FIGS. 2A and 2B compare the Cdc2 kinase activity in *P. carinii* trophozoites and cysts. A. *P. carinii* trophozoites. B. *P. carinii* cysts.

To determine whether Cdc2 activity was regulated over the life cycle of the organism, *P. carinii* trophozoites and cysts were separated by differential filtration, lysed, and equal amounts of extracted proteins (550 μg each) assayed for Cdc2-like protein kinase activity following immunoprecipitation with anti-PSTAIR antibody and using histone H1 as substrate, as described in Example 2. It was found that *P. carinii* trophozoites had greater Cdc2-like protein kinase activity, as evidenced by substantial phosphorylation of histone H1 (see FIG. 2, panel A). Activity was also detected in cyst extracts, but at a lower level (see FIG. 2, panel B). This indicates that Cdc2-like activity is regulated during the life cycle of *P. carinii.*

Example 4

Cloning of the *P. carinii* cdc2 gene and cDNA sequences

*P. carinii* was isolated from lungs of immunosuppressed rats as described in Example 1. Genomic DNA was extracted and amplified with degenerate primers to conserved amino-acid motifs from other fungal Cdc2 proteins. The A+T rich (>65%) coding bias for *P. carinii* was incorporated into the design of the oligonucleotide primers to limit the degree of degeneracy in the third position of each codon. The first primer (TTC (A/T/C/G)CG($^{A}/_{T}$)AT($^{A}/_{T}$)GC($^{A}/_{T}$)GT($^{A}/_{G}$)CT ($^{A}/_{T}$)G (SEQ ID NO:12) was from the conserved PSTAIR region; the second primer (GG($^{A}/_{T}$)GAAGG($^{A}/_{T}$)AC($^{A}/_{T}$) TATGG($^{A}/_{T}$)GT($^{A}/_{T}$)G) (SEQ ID NO:13) was from the ATP-binding region. Thirty cycles of denaturation at 94° C. for 1 minute, annealing at 48° C. for 1 minute, and elongation at 72° C. for 1 minute, was performed with 1 μM of each primer.

A single 123 bp (SEQ ID NO:14) product was generated, subcloned into a pCRII vector (Invitrogen) and sequenced. The 123 bp product corresponds to nucleotides 30–152 in the genomic sequence set out in FIG. 4B. The sequence was compared to all sequences in GenBank using the BLAST genetic analysis program (National Center for Biotechnology Information). The sequence was found to be unique in the GenBank and EMBL analysis, but was 75% homologous to the corresponding PSTAIR cdc2 sequence from *Schizosaccharomyces pombe* and structurally similar to cdc2 sequences from other fungi.

To confirm the PCR product was of *P. carinii* origin, it was hybridized to a nitrocellulose membrane containing *P. carinii* chromosomes separated by contour-clamped homogenous field electrophoresis (CHEF). The product was labeled with [$^{32}$P]-α-dATP (Amersham) by the random primer method (Rediprime System, Amersham). After prehybridization for 30 minutes in ExpressHyb solution (Clontech), the CHEF membrane was incubated at 60° C. for one hour with 1.5×10$^{6}$ cpm/ml of the labeled product. The membrane was washed with 2× SSC containing 0.05% SDS at 37° C. for 40 minutes and with 2× SSC containing 0.1% SDS at 50° C. for 40 minutes, then examined by autoradiography. The PCR product hybridized to a single *P. carinii* chromosome under moderate stringency conditions, suggesting the cdc2 gene resides on a single chromosome (see FIG. 3C).

A full length genomic *P. carinii* cdc2 clone was obtained by screening a rat-derived *P. carinii* λgt11 genomic library (obtained from Dr. James R. Stringer, University of Cincinnati College of Medicine) by hybridization to the 123 bp PCR product. Clones were plaque-purified to homogeneity. A 2.7 kB insert was identified, subcloned into pGEM-7Zf(−) (Promega) and both stands fully sequenced (see FIG. 3B). *P. carinii* cdc2 cDNA was produced by reverse-transcribing 10 μg of total RNA extracted from *P. carinii* by guanadinium isothiocyanate with 1.5 μM oligo-dT (15-mer) and 400 U of M-MLV reverse transcriptase. After an initial four minute hot start at 94° C., the cDNA was amplified with 30 cycles of denaturation at 94° C. for 1 minute, annealing at 56° C. for 1 minute, elongation at 72° C. for 1 minute, and a final 72° C. ten minute extension with 1 μM of primers (TTTTCATATGGAGCAATATCAGAGGTTAGAG (SEQ ID NO:15), containing a 5' NdeI site, and TTTTGGATCCCTATAGCACCACATTAGATCTATT (SEQ ID NO:16), containing a 3' BamHI site). A single 900 bp product was subcloned into pCRII and sequenced.

Figure 3B:
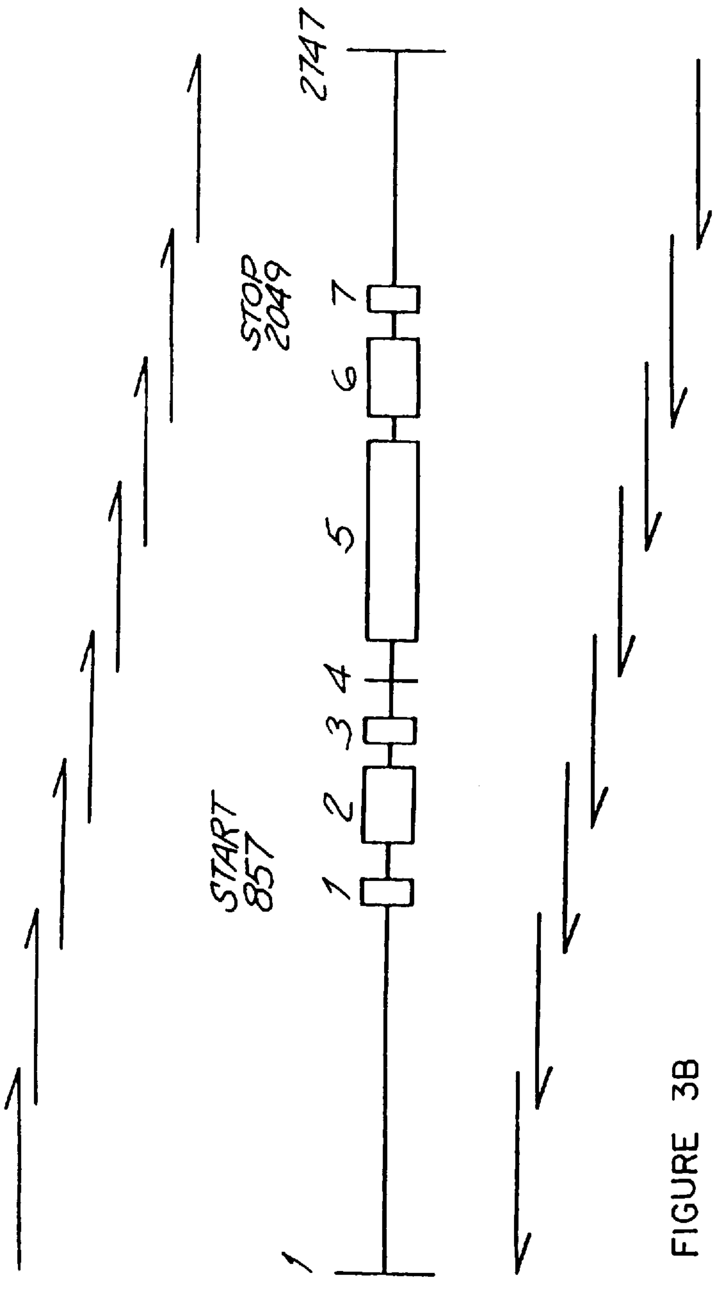
FIG. 3B is a diagram of the organization of the *P. carinii* genomic clone. The *P. carinii* cdc2 genomic clone was sequenced using overlapping primers as shown. Seven exons (boxed) were predicted.
Figure 3C:
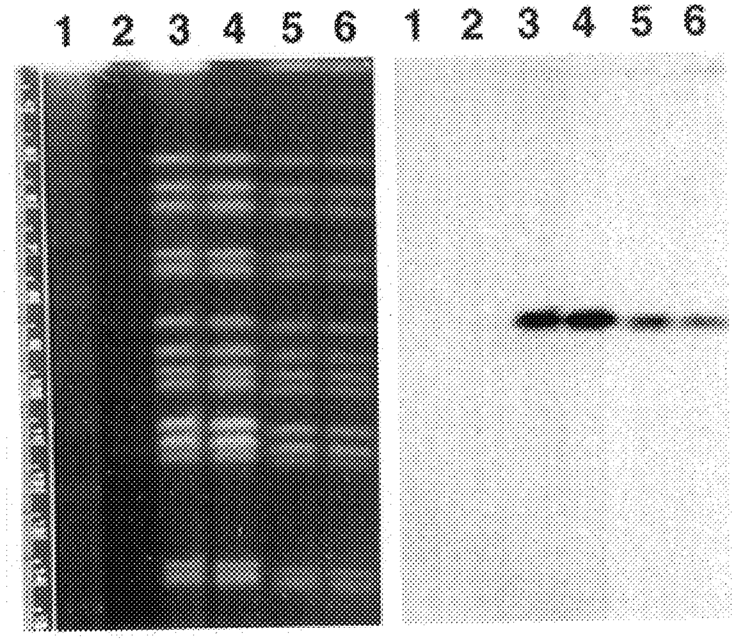
FIG. 3C is the hybridization of the PCR product to a single chromosome from *P. carinii*. A 123-bp *P. carinii* cdc2 probe obtained by PCR (see below) was hybridized to a single *P. carinii* chromosome under high stringency conditions. Lane 1 is a lambda DNA ladder, lanes 3–6 are *P. carinii* chromosomes resolved by contour-clamped homogenous field electrophoresis (CHEF).

The *P. carinii* cdc2 gene is composed of seven exons and six introns containing an open reading frame encoding 300 amino acids (see FIG. 3B). The molecular mass predicted from this sequence was 34,430 Daltons. Exon 2 contains regions encoding the conserved PSTAIR domain. The sequence of the complete cdc2 gene was compared against GenBank and found to be unique. BlastN comparison at the nucleotide level indicated that *Candida albicans* (SEQ ID NO:18) was the closest, with 72% identity. *Ajellomyces capsulata* (SEQ ID NO:20), formerly known as Histoplasma capsulata, was 78% identical at the amino acid level as determined by BlastP analysis. After translation into six reading frames, BlastX analysis indicated that *Oryza sativa* (rice (SEQ ID NO:26)) was the closest with 61% identity (see FIG. 4A).

A 6.3% discrepancy in nucleotide sequence was observed comparing the genomic sequence, derived from the University of Cincinnati genomic library, to the cDNA sequence. The RNA used to prepare the cDNA was taken from *P. carinii* obtained from the rat colony housed in the Mayo Clinic Animal Care Facility (see FIG. 4B). The minor differences most likely reflect strain variation between the two *P. carinii* sources. All but one of the differences are associated with preserving the putative polypeptide sequence. A single amino acid substitution of isoleucine for leucine was detected near the carboxyl-terminus of the molecule, a region not generally associated with enzymatic activity.

Example 5

Determination of *P. carinii* cdc2 activity in fungal cell cycle progression

The functional capacity of *P. carinii* Cdc2 in cell cycle control was analyzed by transforming a Cdc2-deficient *Schizosaccharomyces pombe* with the *P. carinii* cdc2 cDNA. The *S. pombe* cdc2 mutants are temperature sensitive (ts) and grow at the permissive temperature of 30° C., but undergo cell cycle arrest in late G2 at the non-permissive temperature of 37° C. due to the instability of the mutated *S. pombe* Cdc2.

*P. carinii* cdc2 cDNA was excised from pCRII by digestion with NdeI and BamHI, and directionally subcloned into the episomal yeast expression vector pREP41. This plasmid contains a leu2 gene that allows growth of transformants on media lacking leucine and a *S. pombe* nmt1 promoter that is expressed in the absence of thiamine. *S. pombe* ts-cdc2 mutants were grown to mid-log phase, $OD_{595}$ approximately 0.5, in YES media (0.5% yeast extract, 3% D-glucose, 150

Figure 5:
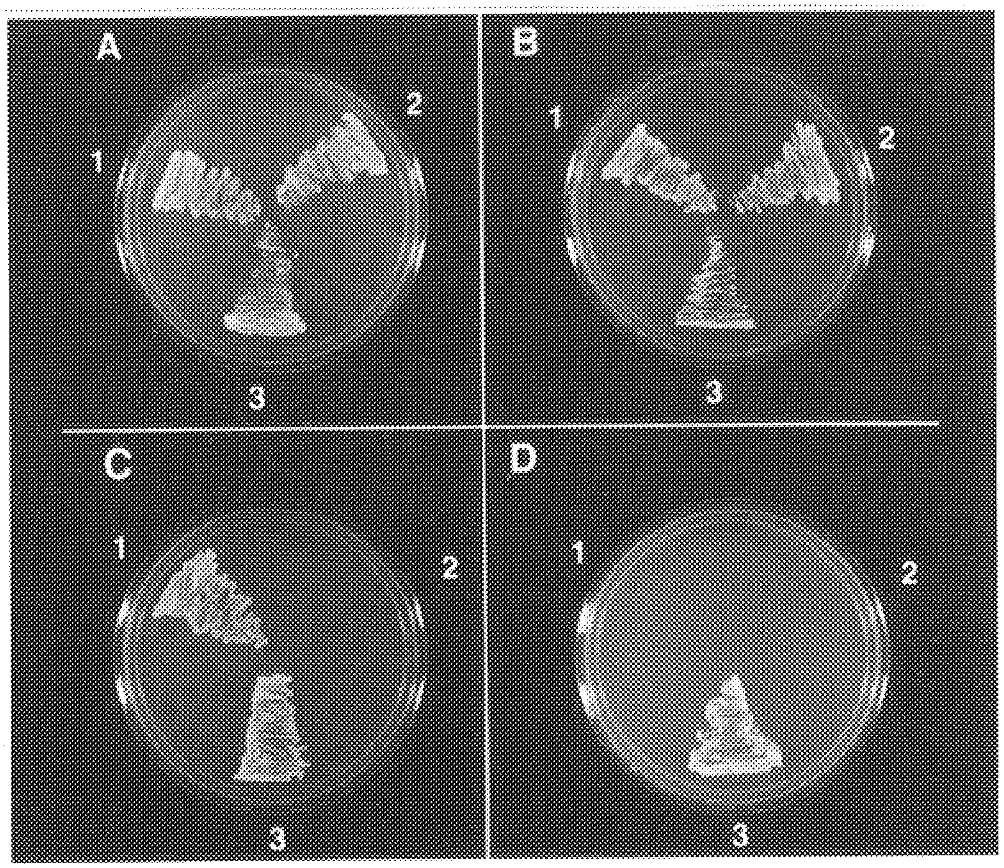
FIGS. 5A–5D are plates streaked with *S. pombe*. The orientation of each plate is the same. (1) *S. pombe* mutants expressing temperature-sensitive Cdc2 transformed with *P. carinii* cdc2 cDNA cloned into pREP41 (clone 14). (2) *S. pombe* mutants transformed with pREP41 vector alone. (3) *S. pombe* mutants transformed with the pIRT2 vector containing wild type *S. pombe* cdc2. A. Plates incubated at the permissive temperature of 30° C. in the absence of thiamine. B. Incubation at 30° C. in the presence of thiamine (10 μM). C. Identical plates incubated at 37° C. in the absence of thiamine. D. Incubation of plates at 37° C. in the presence of thiamine.

$\mu$g/L each adenine, histidine, leucine, uracil, and lysine hydrochloride) at 30° C. The mutants were transformed by electroporation with 1 $\mu$g of pREP41 vector containing *P. carinii* cdc2 cDNA or with pREP41 vector alone or with pIRT2 vector containing *S. pombe* wild-type cdc2 cDNA. Transformants were plated in the absence of leucine and thiamine, grown at 30° C. and 37° C., and assessed for their ability to proliferate. The vector-only controls failed to proliferate, whereas transformants with the *P. carinii* cdc2 or *S. pombe* wild-type cdc2 gene were able to proliferate (see FIG. 5).

The presence of the *P. carinii* cdc2 gene was verified in *P. carinii* cdc2-complemented colonies growing at 37° C. by isolating and sequencing plasmid DNA from cultures grown to mid-log phase in leucine- and thiamine-deficient broth. As an additional control, transformants incubated in the presence of 10 $\mu$M thiamine to repress the pREP41 nmt promoter and inhibit the expression of the *P. carinii* cdc2 cDNA failed to thrive at the non-permissive temperature.

This indicates that the *P. carinii* cdc2 cDNA encodes a fully functional Cdc2 protein that can complement and support the growth of temperature sensitive Cdc2 mutant *S. pombe*, even under non-permissive growth conditions. These data confirm that *P. carinii* cdc2 is active in promoting fungal cell cycle completion.

Example 6

Antibody with specific binding affinity for the carboxyl-terminus of *P. carinii* Cdc2

A unique 11 amino acid sequence (amino acids 290–300 of the amino acid sequence described in FIGS. 3 and 4) was identified at the carboxy-terminus of *P. carinii* through computer analysis (NCBI search of GenBank and the EMBO databases). Blast-P analysis revealed that this sequence was not conserved in other known proteins and was entirely unique in comparison to human, rat, and all other Cdc2 proteins.

An 11 amino acid peptide (NH2-(Cys)-Phe-Ile-Asn-Leu-Asn-Arg-Ser-Asn-Val-Val-Leu-COOH) (SEQ ID NO:17) was synthesized. The amino-terminal cysteine is not natively present and was added for convenience in coupling the synthetic peptide to the carrier.

After coupling the peptide to Keyhole Limpet Hemocyanin, New Zealand White rabbits were immunized. A resulting polyclonal antibody was affinity purified over a cognate peptide column. The column was created by coupling the cognate peptide to sulfo-link gel (Pierce Chemical Company, Rockford, Ill.) according to the manufacturer's instructions. After passing serum through the column, the column was washed with 50 mM Tris/150 mM NaCl, pH 7.4. Antibody was eluted from the column with 0.2M glycine, pH 2.3 and subsequently dialyzed against 50 mM Tris/150 mM NaCl pH 7.4.

Figure 6:
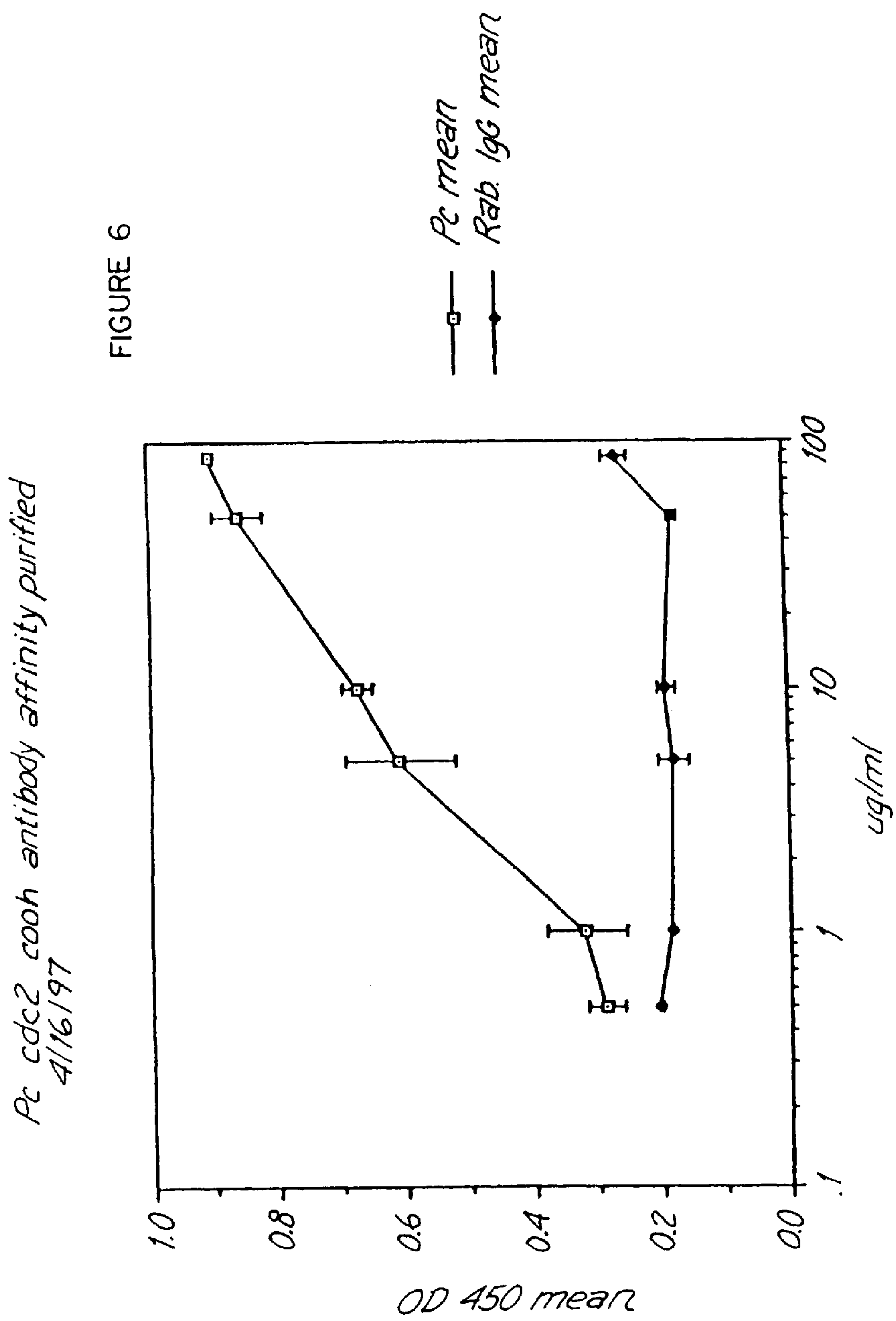
FIG. 6 is a graph of the results from an ELISA experiment using affinity purified antibody and the C-terminal polypeptide.

The antibody was characterized by an ELISA, as shown in FIG. 6. The antibody has specific affinity for a 34 kDa protein from *P. carinii* extracts, consistent with the predicted molecular weight of *P. carinii* Cdc2. Immunoprecipitated *P. carinii* Cdc2 protein has the ability to phosphorylate histone H1 in vitro. Uninfected rat lung extracts do not yield any significant precipitation products nor Histone H1 kinase activity when studied under identical condition. No cross-reactivity between the antibody and Cdc2 protein from rats was observed.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying an agent inhibiting the phosphorylation activity of *P. carinii* cdc2 polypeptide, comprising incubating an isolated Cdc2 polypeptide and a substrate of Cdc2 polypeptide with said agent to determine if phosphorylation of said substrate is inhibited.

2. The method of claim 1, wherein said isolated Cdc2 polypeptide is recombinant Cdc2 polypeptide.

3. The method of claim 1, wherein said isolated Cdc2 polypeptide comprises the amino acid sequence of SEQ ID NO:11.

4. The method of claim 1, wherein said substrate is selected from the group consisting of H1 histone, Cdc25 polypeptide, nuclear lamins, retinoblastoma protein, cyclin B and DNA polymerase alpha.

5. The method of claim 4, wherein said substrate is H1 histone.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 2747 base pairs
( B ) TYPE: nucleic acid
( C ) STRANDEDNESS: single
( D ) TOPOLOGY: linear ( i i ) MOLECULE TYPE: Genomic DNA ( i x ) FEATURE:
( A ) NAME/KEY: Coding Sequence
( B ) LOCATION: 857...893
( D ) OTHER INFORMATION:
( A ) NAME/KEY: Coding Sequence
( B ) LOCATION: 942...1096
( D ) OTHER INFORMATION:
( A ) NAME/KEY: Coding Sequence
( B ) LOCATION: 1147...1194
( D ) OTHER INFORMATION:
( A ) NAME/KEY: Coding Sequence
( B ) LOCATION: 1242...1254
( D ) OTHER INFORMATION:
( A ) NAME/KEY: Coding Sequence
( B ) LOCATION: 1311...1706

-continued ( D ) OTHER INFORMATION:
( A ) NAME/KEY: Coding Sequence
( B ) LOCATION: 1751...1891
( D ) OTHER INFORMATION:
( A ) NAME/KEY: Coding Sequence
( B ) LOCATION: 1944...2048
( D ) OTHER INFORMATION:

( xi ) SEQUENCE DESCRIPTION: SEQ ID NO:1:

GTCATTTTTA TATGATAAAT ATGTTTCTCT TTCTAACGAT TTCTTTGCTA TAATAATATC 60

ATTCTGAATA TCTTCTATCA ATAATTCTAC TTTATTTAAA AGACAGATCT AAATTAAAAT 120

TGTGTTACTT TTAGATATAT AATTGCGTTC TGGCCTTATA AAACCCATTA TTAATAATCT 180

TATTTCTTGA TCATAGAAAT CGCATTTAAA TTTATGTATA AAATGTACTT CCTAAATCTT 240

TTTAAAACAA ACCTTTTTGT AATGAACATA CTGCTGACAA TTTCTGGTTC TTATAATACG 300

GATTCCATCC CACGCTCATG ACCATTATAT AGACGCTATC GTCACCCTCT ATCATTACTC 360

GACCCCAGCC ATAATAAATT CCTGTTTTTG AATATAGAAA TTTTGGAATA TTTTCTTCTG 420

AAATATTTGC TAAAACATAT CAATTTATGT ATATTCTTTA TTTATACCTG TTGGTATTTC 480

CAATTCACTT CTTCCTCTAC CATATCCCTT GACCACCTAT ATTTTTAACA ATACTAAAAA 540

AATACTATTA AAATTTACTA ACTTTTCCTT TCAAATAAAT AGGATAAGGG TATTCAGGAC 600

CTGAATCTGG CCCTGAATTA TTTTCTAATT CTATCTCCAT ATCTGCCATT CTACAAAAAT 660

TTTCAAATAT CTACAAGACT TTAAACAACT ATAACCCTTT TAAACATAAA TATCAATATC 720

CCTCGCTTTT CTTACATTAA TGCTGAGCTT TTAAGTAAAA ATATTGTCTT TCTATATATT 780

ATCTTACCCT CTCACTAGAA AATATCACGT GACATTGACA TAATAACAAC GTATTTTGAA 840

AATAACGAGG TAAACT ATG GAG CAA TAT CAG AGG TTA GAG AAG ATT GGA GAA 892
Met Glu Gln Tyr Gln Arg Leu Glu Lys Ile Gly Glu
1 5 10

G GCATAAAAAC CTATATTTAT AGAGTTTGCG CTTATTTGCA TTTAAGGG ACT TAT 947
Gly Thr Tyr
1

GGA GTT GTT TAT AAG GCC AAG GAT CTT GAA AGT GGC ACA ATT GTA GCT 995
Gly Val Val Tyr Lys Ala Lys Asp Leu Glu Ser Gly Thr Ile Val Ala
5 10 15

CTT AAA AAA ATC CGG TTA GAG GCA GAA GAT GAG GGA GTT CCT AGC ACA 1043
Leu Lys Lys Ile Arg Leu Glu Ala Glu Asp Glu Gly Val Pro Ser Thr
20 25 30

GCA ATT CGT GAA ATA TCT CTT TTG AAA GAA ATG CAC AAT GAT AAT GTC 1091
Ala Ile Arg Glu Ile Ser Leu Leu Lys Glu Met His Asn Asp Asn Val
35 40 45 50

GTA AG GTATCA TTTTGCTGTA TTTTTTTTCA CGGGGTTTTT ATGGGTCAAT TAGA 1146
Val Arg

CTT TTG AAT ATT ATT CAT CAG GAA TCA CGT CTA TAT CTT GTT TTT GAA 1194
Leu Leu Asn Ile Ile His Gln Glu Ser Arg Leu Tyr Leu Val Phe Glu
1 5 10 15

GTAGGTTTCT TTTCTTTTCA TGAATGTTTC TCATTTTGTT GTATTAG TTT CTT GAT 1250
Phe Leu Asp
1

CTT GAT AA TTCTTATATA TATATACATA ATATATATAT ATATTCATAT ATTATGTTAG 1308
Leu Asp
5

AT TTG AAA AAA TAT ATG AAT AGT ATT CCA AAA GAC ATG ATG CTT GGA 1355
Leu Lys Lys Tyr Met Asn Ser Ile Pro Lys Asp Met Met Leu Gly
1 5 10 15

GCT GAA ATG ATC AAA AAA TTT ATG TCT CAA CTT GTA TCA GGT GTT AAA 1403
Ala Glu Met Ile Lys Lys Phe Met Ser Gln Leu Val Ser Gly Val Lys
20 25 30

-continued

```
TAT TGT CAT TCT CAT CGT ATT CTT CAT CGT GAC TTG AAG CCC CAA AAT      1451
Tyr Cys His Ser His Arg Ile Leu His Arg Asp Leu Lys Pro Gln Asn
            35                  40                  45

CTT CTT ATT GAT CGA GAA GGA AAT CTT AAA CTT GCT GAT TTC GGG CTT      1499
Leu Leu Ile Asp Arg Glu Gly Asn Leu Lys Leu Ala Asp Phe Gly Leu
        50                  55                  60

GCT CGG GCA TTT GGT GTT CCT TTA CGT GGT TAT ACT CAT GAG GTT GTT      1547
Ala Arg Ala Phe Gly Val Pro Leu Arg Gly Tyr Thr His Glu Val Val
    65                  70                  75

ACA CTT TGG TAT CGT GCT CCA GAA GTT CTT TTA GGT GGT CGA CAA TAT      1595
Thr Leu Trp Tyr Arg Ala Pro Glu Val Leu Leu Gly Gly Arg Gln Tyr
80                  85                  90                  95

GCA ACA GCA CTT GAT ATT TGG AGC ATT GGA TGT ATT TTT GCT GAA ATG      1643
Ala Thr Ala Leu Asp Ile Trp Ser Ile Gly Cys Ile Phe Ala Glu Met
                100                 105                 110

GCT ACA AAA AAA CCG TTA TTT CCA GGC GAT TCT GAA ATT GAT GAA ATA      1691
Ala Thr Lys Lys Pro Leu Phe Pro Gly Asp Ser Glu Ile Asp Glu Ile
            115                 120                 125

TTC AGA ATA TTT AGG TCAAGTTTCT GGGTATTAAG TATATAGTTT ATTTATTTTT      1746
Phe Arg Ile Phe Arg
        130

CAGA ATA TTA GGA ACA CCT GAT GAA AAT TCT TGG CCT GGT ATT ACA TCA     1795

     Ile Leu Gly Thr Pro Asp Glu Asn Ser Trp Pro Gly Ile Thr Ser
      1               5                  10                  15

TAT CCT GAT TTT AAA GCA ACT TTT CCC AAA TGG TCA CCA AAA AAT CTT      1843
Tyr Pro Asp Phe Lys Ala Thr Phe Pro Lys Trp Ser Pro Lys Asn Leu
                20                  25                  30

GGA GAA TTA ATT ACA GAA CTT GAT AGT GAT GGA ATA GAT TTA TTA CAG      1891
Gly Glu Leu Ile Thr Glu Leu Asp Ser Asp Gly Ile Asp Leu Leu Gln
            35                  40                  45

GTTTTCTATT TACAATATAG ATTATTAAAA AATAACAATG ATAACTATGT AG AAA        1946
                                                          Lys
                                                           1

TGT CTC AGA TAT TAT CCT GCT GAA CGT ATT AGT GCA AAA AAG GCT CTC      1994
Cys Leu Arg Tyr Tyr Pro Ala Glu Arg Ile Ser Ala Lys Lys Ala Leu
            5                   10                  15

GAT CAT CCA TAT TTT GAT GAT TTC ATT AAT CTC AAT AGA TCT AAT GTG      2042
Asp His Pro Tyr Phe Asp Asp Phe Ile Asn Leu Asn Arg Ser Asn Val
        20                  25                  30

GTG CTA TAGTTTTTAT CATTGGTCAT TATATAATTT AAGGGTATTT ATATCAACTT       2098
Val Leu
    35

AATTTCTTCT TTTTAACCTA ATAGATCTTT AATTTTAAAA ATTGTCTATT ATAAATAATA    2158

GATAAGTAAA TATCTTTGTA AATGATTTTC GCAGATATTG TATAACTATA TTGGCTATAA    2218

AATTCATTCA ATTGATTCAT AATTTAAATA CATTGTAATA TTAAATTAAC ATTTCTTTAA    2278

ATATCTTTAT GACAGTATTT TCCGGATATA TTTGATAATT TGCTTATAAA ACATATGATT    2338

TTTAGATAAA TATTTAACAG CCGTATTTAA CAGAGAGATT CAACCAAAAG GGTTCTATTA    2398

AGCTATAAAG TCTATTTGAT ATCTAAATTT GAAAAAACTA TTTAATAATA AATTGTCATT    2458

TAAAAATGTC CAGTATTTCA GAGAGAAAGA TGGATATAAA GAGCTTAGCA GGAGCATCTG    2518

GTCCTGGATA TTCAGATGTG TCTTTAAAAT GCAGAAAATG TAAAAGTTAT GAGGAAATAT    2578

TGGATAATAA TGAGCCATCT CAAAAACAAG CCAATAATGA CCCAGAAAAA AGGAATATTT    2638

CTGGTTCTTT TGAAAGACAT CATAGAGAAA GAGGCTATAG TCAGAATTGC TATGCCTGCA    2698

GATCTTCAGT TTCCCCAAAA TCTCATCAAA TGACGAGATT TAATGAACG                2747
```

( 2 ) INFORMATION FOR SEQ ID NO:2:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:2:

Met Glu Gln Tyr Gln Arg Leu Glu Lys Ile Gly Glu Gly
1 5 10

( 2 ) INFORMATION FOR SEQ ID NO:3:

( i ) SEQUENCE CHARACTERISTICS:
( A ) LENGTH: 52 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:3:

Thr Tyr Gly Val Val Tyr Lys Ala Lys Asp Leu Glu Ser Gly Thr Ile
1 5 10 15

Val Ala Leu Lys Lys Ile Arg Leu Glu Ala Glu Asp Glu Gly Val Pro
20 25 30

Ser Thr Ala Ile Arg Glu Ile Ser Leu Leu Lys Glu Met His Asn Asp
35 40 45

Asn Val Val Arg
50

( 2 ) INFORMATION FOR SEQ ID NO:4:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:4:

Leu Leu Asn Ile Ile His Gln Glu Ser Arg Leu Tyr Leu Val Phe Glu
1 5 10 15

( 2 ) INFORMATION FOR SEQ ID NO:5:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:5:

Phe Leu Asp Leu Gly
1 5

( 2 ) INFORMATION FOR SEQ ID NO:6:

( i ) SEQUENCE CHARACTERISTICS:
( A ) LENGTH: 132 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:6:

```
Leu Lys Lys Tyr Met Asn Ser Ile Pro Lys Asp Met Met Leu Gly Ala
 1               5                  10                  15
Glu Met Ile Lys Lys Phe Met Ser Gln Leu Val Ser Gly Val Lys Tyr
            20                  25                  30
Cys His Ser His Arg Ile Leu His Arg Asp Leu Lys Pro Gln Asn Leu
        35                  40                  45
Leu Ile Asp Arg Glu Gly Asn Leu Lys Leu Ala Asp Phe Gly Leu Ala
    50                  55                  60
Arg Ala Phe Gly Val Pro Leu Arg Gly Tyr Thr His Glu Val Val Thr
65                  70                  75                  80
Leu Trp Tyr Arg Ala Pro Glu Val Leu Leu Gly Gly Arg Gln Tyr Ala
                85                  90                  95
Thr Ala Leu Asp Ile Trp Ser Ile Gly Cys Ile Phe Ala Glu Met Ala
            100                 105                 110
Thr Lys Lys Pro Leu Phe Pro Gly Asp Ser Glu Ile Asp Glu Ile Phe
        115                 120                 125
Arg Ile Phe Arg
    130
```

( 2 ) INFORMATION FOR SEQ ID NO:7:

( i ) SEQUENCE CHARACTERISTICS:
( A ) LENGTH: 47 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:7:

```
Ile Leu Gly Thr Pro Asp Glu Asn Ser Trp Pro Gly Ile Thr Ser Tyr
 1               5                  10                  15
Pro Asp Phe Lys Ala Thr Phe Pro Lys Trp Ser Pro Lys Asn Leu Gly
            20                  25                  30
Glu Leu Ile Thr Glu Leu Asp Ser Asp Gly Ile Asp Leu Leu Gln
        35                  40                  45
```

( 2 ) INFORMATION FOR SEQ ID NO:8:

( i ) SEQUENCE CHARACTERISTICS:
( A ) LENGTH: 35 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:8:

Lys Cys Leu Arg Tyr Tyr Pro Ala Glu Arg Ile Ser Ala Lys Lys Ala
1 5 10 15

Leu Asp His Pro Tyr Phe Asp Asp Phe Ile Asn Leu Asn Arg Ser Asn
20 25 30

Val Val Leu
35

( 2 ) INFORMATION FOR SEQ ID NO:9:

( i ) SEQUENCE CHARACTERISTICS:
( A ) LENGTH: 903 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: Coding Sequence
( B ) LOCATION: 1...900
( D ) OTHER INFORMATION:

( x i ) SEQUENCE DESCRIPTION: SEQ ID NO:9:

ATG GAG CAA TAT CAG AGG TTA GAG AAG ATT GGA GAA GGA ACT TAT GGA 48
Met Glu Gln Tyr Gln Arg Leu Glu Lys Ile Gly Glu Gly Thr Tyr Gly
1 5 10 15

GTT GTT TAT AAA GCA AAG GAT CTT GAA AGT GGT ACA ATT GTA GCT CTT 96
Val Val Tyr Lys Ala Lys Asp Leu Glu Ser Gly Thr Ile Val Ala Leu
20 25 30

AAG AAA ATC CGA TTA GAA GCA GAA GAT GAG GGA GTT CCT AGT ACA GCA 144
Lys Lys Ile Arg Leu Glu Ala Glu Asp Glu Gly Val Pro Ser Thr Ala
35 40 45

ATT CGT GAG ATA TCA CTT TTG AAA GAG ATG CAC AAT GAT AAT GTT GTA 192
Ile Arg Glu Ile Ser Leu Leu Lys Glu Met His Asn Asp Asn Val Val
50 55 60

AGA CTT TTG AAT ATA ATT CAT CAA GAG TCA CGT TTA TAT CTT GTT TTT 240
Arg Leu Leu Asn Ile Ile His Gln Glu Ser Arg Leu Tyr Leu Val Phe
65 70 75 80

GAA TTT CTT GAT CTT GAT TTA AAA AAG TAT ATG AAT AGT ATT CCA AAG 288
Glu Phe Leu Asp Leu Asp Leu Lys Lys Tyr Met Asn Ser Ile Pro Lys
85 90 95

GAC ATG ATG CTT GGT GCA GAA ATG ATT AAA AAG TTT ATG TCA CAA CTT 336
Asp Met Met Leu Gly Ala Glu Met Ile Lys Lys Phe Met Ser Gln Leu
100 105 110

GTA TCA GGT GTT AAA TAT TGT CAT TCT CAT CGT ATT CTT CAT CGT GAC 384
Val Ser Gly Val Lys Tyr Cys His Ser His Arg Ile Leu His Arg Asp
115 120 125

TTG AAA CCA CAA AAT CTT CTT ATA GAT CGA GAA GGA AAT CTT AAA TTA 432
Leu Lys Pro Gln Asn Leu Leu Ile Asp Arg Glu Gly Asn Leu Lys Leu
130 135 140

GCA GAT TTT GGG CTT GCA AGG GCG TTT GGT GTT CCA TTG CGT GGT TAT 480
Ala Asp Phe Gly Leu Ala Arg Ala Phe Gly Val Pro Leu Arg Gly Tyr
145 150 155 160

ACT CAT GAA GTT GTT ACA CTT TGG TAT CGT GCT CCA GAA GTT CTT TTA 528
Thr His Glu Val Val Thr Leu Trp Tyr Arg Ala Pro Glu Val Leu Leu
165 170 175

GGT GGT CGA CAA TAT GCA ACA GCG CTT GAT ATA TGG AGC ATT GGA TGT 576
Gly Gly Arg Gln Tyr Ala Thr Ala Leu Asp Ile Trp Ser Ile Gly Cys
180 185 190

ATT TTT GCA GAA ATG GCT ACA AAA AAG CCA TTA TTT CCA GGT GAT TCT 624
Ile Phe Ala Glu Met Ala Thr Lys Lys Pro Leu Phe Pro Gly Asp Ser
195 200 205

-continued

GAA ATT GAT GAA ATA TTT AGA ATA TTT AGA ATA TTA GGG ACT CCA GAT 672
Glu Ile Asp Glu Ile Phe Arg Ile Phe Arg Ile Leu Gly Thr Pro Asp
210 215 220

GAA AAT TCT TGG CCT GGT ATT ACA TCT TAT CCG GAT TTT AAG GCA ACT 720
Glu Asn Ser Trp Pro Gly Ile Thr Ser Tyr Pro Asp Phe Lys Ala Thr
225 230 235 240

TTT CCA AAA TGG TCA CCA AAA AAT CTT GGA GAA TTA ATT ACA GAA CTT 768
Phe Pro Lys Trp Ser Pro Lys Asn Leu Gly Glu Leu Ile Thr Glu Leu
245 250 255

GAT AGT GAT GGA ATA GAT TTA TTA CAG AAA TGT CTT AGA TAT TAT CCT 816
Asp Ser Asp Gly Ile Asp Leu Leu Gln Lys Cys Leu Arg Tyr Tyr Pro
260 265 270

GCT GAA CGT ATT AGC GCT AAA AAA GCT CTC GAT CAT CCT TAT TTT GAT 864
Ala Glu Arg Ile Ser Ala Lys Lys Ala Leu Asp His Pro Tyr Phe Asp
275 280 285

GAT TTC ATT AAT ATC AAT AGA TCT AAT GTG GTG CTA TAG 903
Asp Phe Ile Asn Ile Asn Arg Ser Asn Val Val Leu
290 295 300

( 2 ) INFORMATION FOR SEQ ID NO:10:

( i ) SEQUENCE CHARACTERISTICS:
( A ) LENGTH: 300 amino acids
( B ) TYPE: amino acid
( C ) STRANDEDNESS: single
( D ) TOPOLOGY: linear ( i i ) MOLECULE TYPE: protein ( v ) FRAGMENT TYPE: internal ( x i ) SEQUENCE DESCRIPTION: SEQ ID NO:10:

Met Glu Gln Tyr Gln Arg Leu Glu Lys Ile Gly Glu Gly Thr Tyr Gly
1 5 10 15

Val Val Tyr Lys Ala Lys Asp Leu Glu Ser Gly Thr Ile Val Ala Leu
20 25 30

Lys Lys Ile Arg Leu Glu Ala Glu Asp Glu Gly Val Pro Ser Thr Ala
35 40 45

Ile Arg Glu Ile Ser Leu Leu Lys Glu Met His Asn Asp Asn Val Val
50 55 60

Arg Leu Leu Asn Ile Ile His Gln Glu Ser Arg Leu Tyr Leu Val Phe
65 70 75 80

Glu Phe Leu Asp Leu Asp Leu Lys Lys Tyr Met Asn Ser Ile Pro Lys
85 90 95

Asp Met Met Leu Gly Ala Glu Met Ile Lys Lys Phe Met Ser Gln Leu
100 105 110

Val Ser Gly Val Lys Tyr Cys His Ser His Arg Ile Leu His Arg Asp
115 120 125

Leu Lys Pro Gln Asn Leu Leu Ile Asp Arg Glu Gly Asn Leu Lys Leu
130 135 140

Ala Asp Phe Gly Leu Ala Arg Ala Phe Gly Val Pro Leu Arg Gly Tyr
145 150 155 160

Thr His Glu Val Val Thr Leu Trp Tyr Arg Ala Pro Glu Val Leu Leu
165 170 175

Gly Gly Arg Gln Tyr Ala Thr Ala Leu Asp Ile Trp Ser Ile Gly Cys
180 185 190

Ile Phe Ala Glu Met Ala Thr Lys Lys Pro Leu Phe Pro Gly Asp Ser
195 200 205

Glu Ile Asp Glu Ile Phe Arg Ile Phe Arg Ile Leu Gly Thr Pro Asp

```
        210                     215                     220

Glu Asn Ser Trp Pro Gly Ile Thr Ser Tyr Pro Asp Phe Lys Ala Thr
225                 230                     235                 240

Phe Pro Lys Trp Ser Pro Lys Asn Leu Gly Glu Leu Ile Thr Glu Leu
                245                     250                     255

Asp Ser Asp Gly Ile Asp Leu Leu Gln Lys Cys Leu Arg Tyr Tyr Pro
            260                     265                     270

Ala Glu Arg Ile Ser Ala Lys Lys Ala Leu Asp His Pro Tyr Phe Asp
        275                 280                     285

Asp Phe Ile Asn Ile Asn Arg Ser Asn Val Val Leu
    290                     295                     300
```

( 2 ) INFORMATION FOR SEQ ID NO:11:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:11:

```
Phe Ile Asn Leu Asn Arg Ser Asn Val Val Leu
 1               5                  10
```

( 2 ) INFORMATION FOR SEQ ID NO:12:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( x i ) SEQUENCE DESCRIPTION: SEQ ID NO:12:

```
TTCNCGWATW GCWGTRCTWG                                          20
```

( 2 ) INFORMATION FOR SEQ ID NO:13:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( x i ) SEQUENCE DESCRIPTION: SEQ ID NO:13:

```
GGWGAAGGWA CWTATGGWGT WG                                       22
```

( 2 ) INFORMATION FOR SEQ ID NO:14:

( i ) SEQUENCE CHARACTERISTICS:
( A ) LENGTH: 123 base pairs
( B ) TYPE: nucleic acid
( C ) STRANDEDNESS: single
( D ) TOPOLOGY: linear ( i i ) MOLECULE TYPE: Other ( x i ) SEQUENCE DESCRIPTION: SEQ ID NO:14:

```
TGGAGAAGGA ACTTATGGAG TTGTTTATAA AGCAAAGGAT CTTGAAAGTG GTACAATTGT    60

AGCTCTTAAG AAAATCCGAT TAGAAGCAGA AGATGAGGGA GTTCCTAGTA CAGCAATTCG   120
```

TGA 123

(2) INFORMATION FOR SEQ ID NO:15:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: Oligonucleotide (xi) SEQUENCE DESCRIPTION: SEQ ID NO:15:

TTTTCATATG GAGCAATATC AGAGGTTAGA G 31

(2) INFORMATION FOR SEQ ID NO:16:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: Oligonucleotide (xi) SEQUENCE DESCRIPTION: SEQ ID NO:16:

TTTTGGATCC CTATAGCACC ACATTAGATC TATT 34

(2) INFORMATION FOR SEQ ID NO:17:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:17:

Cys Phe Ile Asn Leu Asn Arg Ser Asn Val Val Leu
1 5 10

(2) INFORMATION FOR SEQ ID NO:18:

(i) SEQUENCE CHARACTERISTICS:
(A) LENGTH: 317 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:18:

Met Val Glu Leu Ser Asp Tyr Gln Arg Gln Glu Lys Val Gly Glu Gly
1 5 10 15

Thr Tyr Gly Val Val Tyr Lys Ala Leu Asp Thr Lys His Asn Asn Arg
20 25 30

Val Val Ala Leu Lys Lys Ile Arg Leu Glu Ser Glu Asp Glu Gly Val
35 40 45

Pro Ser Thr Ala Ile Arg Glu Ile Ser Leu Leu Lys Glu Met Lys Asp
50 55 60

Asp Asn Ile Val Arg Leu Tyr Asp Ile Ile His Ser Asp Ser His Lys
65 70 75 80

Leu Tyr Leu Val Phe Glu Phe Leu Asp Leu Asp Leu Lys Lys Tyr Met
85 90 95

Glu Ser Ile Pro Gln Gly Val Gly Leu Gly Ala Asn Met Ile Lys Arg

-continued 100 105 110

Phe Met Asn Gln Leu Ile Arg Gly Ile Lys His Cys His Ser His Arg
115 120 125

Val Leu His Arg Asp Leu Lys Pro Gln Asn Leu Leu Ile Asp Lys Glu
130 135 140

Gly Asn Leu Lys Leu Ala Asp Phe Gly Leu Ala Arg Ala Phe Gly Val
145 150 155 160

Pro Leu Arg Ala Tyr Thr His Glu Val Val Thr Leu Trp Tyr Arg Ala
165 170 175

Pro Glu Ile Leu Leu Gly Gly Lys Gln Tyr Ser Thr Gly Val Asp Met
180 185 190

Trp Ser Val Gly Cys Ile Phe Ala Glu Met Cys Asn Arg Lys Pro Leu
195 200 205

Phe Pro Gly Asp Ser Glu Ile Asp Glu Ile Phe Arg Ile Phe Arg Ile
210 215 220

Leu Gly Thr Pro Asn Glu Glu Ile Trp Pro Asp Val Asn Tyr Leu Pro
225 230 235 240

Asp Phe Lys Ser Ser Phe Pro Gln Trp Lys Lys Lys Pro Leu Ser Glu
245 250 255

Ala Val Pro Ser Leu Asp Ala Asn Gly Ile Asp Leu Leu Asp Gln Met
260 265 270

Leu Val Tyr Asp Pro Ser Arg Arg Ile Ser Ala Lys Arg Ala Leu Ile
275 280 285

His Pro Tyr Phe Asn Asp Asn Asp Asp Arg Asp His Asn Asn Tyr Asn
290 295 300

Glu Asp Asn Ile Gly Ile Asp Lys His Gln Asn Met Gln
305 310 315

( 2 ) INFORMATION FOR SEQ ID NO:19:

( i ) SEQUENCE CHARACTERISTICS:
( A ) LENGTH: 298 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:19:

Met Ser Gly Glu Leu Ala Asn Tyr Lys Arg Leu Glu Lys Val Gly Glu
1 5 10 15

Gly Thr Tyr Gly Val Val Tyr Lys Ala Leu Asp Leu Arg Pro Gly Gln
20 25 30

Gly Gln Arg Val Val Ala Leu Lys Lys Ile Arg Leu Glu Ser Glu Asp
35 40 45

Glu Gly Val Pro Ser Thr Ala Ile Arg Glu Ile Ser Leu Leu Lys Glu
50 55 60

Leu Lys Asp Asp Asn Ile Val Arg Leu Tyr Asp Ile Val His Ser Asp
65 70 75 80

Ala His Lys Leu Tyr Leu Val Phe Glu Phe Leu Asp Leu Asp Leu Lys
85 90 95

Arg Tyr Met Glu Gly Ile Pro Lys Asp Gln Pro Leu Gly Ala Asp Ile
100 105 110

Val Lys Lys Phe Met Met Gln Leu Cys Lys Gly Ile Ala Tyr Cys His
115 120 125

Ser His Arg Ile Leu His Arg Asp Leu Lys Pro Gln Asn Leu Leu Ile
130 135 140

-continued

Asn Lys Asp Gly Asn Leu Lys Leu Gly Asp Phe Gly Leu Ala Arg Ala
145 150 155 160

Phe Gly Val Pro Leu Arg Ala Tyr Thr His Glu Ile Val Thr Leu Trp
165 170 175

Tyr Arg Ala Pro Glu Val Leu Leu Gly Gly Lys Gln Tyr Ser Thr Gly
180 185 190

Val Asp Thr Trp Ser Ile Gly Cys Ile Phe Ala Glu Met Cys Asn Arg
195 200 205

Lys Pro Ile Phe Ser Gly Asp Ser Glu Ile Asp Gln Ile Phe Lys Ile
210 215 220

Phe Arg Val Leu Gly Thr Pro Asn Glu Ala Ile Trp Pro Asp Ile Val
225 230 235 240

Tyr Leu Pro Asp Phe Lys Pro Ser Phe Pro Gln Trp Arg Arg Lys Asp
245 250 255

Leu Ser Gln Val Val Pro Ser Leu Asp Pro Arg Gly Ile Asp Leu Leu
260 265 270

Asp Lys Leu Leu Ala Tyr Asp Pro Ile Asn Arg Ile Ser Ala Arg Arg
275 280 285

Ala Ala Ile His Pro Tyr Phe Gln Glu Ser
290 295

( 2 ) INFORMATION FOR SEQ ID NO:20:

( i ) SEQUENCE CHARACTERISTICS:
( A ) LENGTH: 324 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:20:

Met Glu Asn Tyr Gln Lys Ile Glu Lys Ile Gly Glu Gly Thr Tyr Gly
1 5 10 15

Val Val Tyr Lys Ala Arg Asp Leu Thr His Pro Asn Arg Ile Val Ala
20 25 30

Leu Lys Lys Ile Arg Leu Glu Ala Glu Asp Glu Gly Val Pro Ser Thr
35 40 45

Ala Ile Arg Glu Ile Ser Leu Leu Lys Glu Met His Asp Pro Asn Ile
50 55 60

Val Arg Leu Leu Asn Ile Val His Ala Asp Gly His Lys Leu Tyr Leu
65 70 75 80

Val Phe Glu Phe Leu Asp Leu Asp Leu Lys Lys Tyr Met Glu Ala Leu
85 90 95

Pro Val Ser Glu Gly Gly Arg Gly Lys Ala Leu Pro Asp Gly Ser Thr
100 105 110

Leu Asp Met Asn Arg Leu Gly Leu Gly Glu Ala Met Val Lys Lys Phe
115 120 125

Met Ala Gln Leu Val Glu Gly Ile Arg Tyr Cys His Ser His Arg Val
130 135 140

Leu His Arg Asp Leu Lys Pro Gln Asn Leu Leu Ile Asp Arg Glu Gly
145 150 155 160

Asn Leu Lys Leu Ala Asp Phe Gly Leu Ala Arg Ala Phe Gly Val Pro
165 170 175

Leu Arg Thr Tyr Thr His Glu Val Val Thr Leu Trp Tyr Arg Ala Pro
180 185 190

Glu Ile Leu Leu Gly Gly Arg Gln Tyr Ser Thr Gly Val Asp Met Trp
195 200 205

Ser Val Gly Ala Ile Phe Ala Glu Met Cys Thr Arg Lys Pro Leu Phe
210 215 220

Pro Gly Asp Ser Glu Ile Asp Glu Ile Phe Lys Ile Phe Lys Leu Leu
225 230 235 240

Gly Thr Pro Asp Glu Asn Thr Trp Pro Gly Val Thr Ser Phe Pro Asp
245 250 255

Phe Lys Ala Ser Phe Pro Lys Trp Lys Arg Glu Asp Thr Arg Lys Leu
260 265 270

Val Pro Gly Leu Glu Arg Asn Gly Leu Asp Leu Leu Asp Ala Met Leu
275 280 285

Glu Tyr Asp Pro Ala Arg Arg Ile Ser Ala Lys Gln Ala Cys Met His
290 295 300

Pro Tyr Phe Gln Ala Gly Ser Ser Ala Tyr Ser Gly Arg Glu Arg Leu
305 310 315 320

Gln Pro Tyr Pro ( 2 ) INFORMATION FOR SEQ ID NO:21:

( i ) SEQUENCE CHARACTERISTICS:
( A ) LENGTH: 323 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:21:

Met Glu Asn Tyr Gln Lys Ile Glu Lys Ile Gly Glu Gly Thr Tyr Gly
1 5 10 15

Val Val Tyr Lys Ala Arg Glu Leu Thr His Pro Asn Arg Ile Val Ala
20 25 30

Leu Lys Lys Ile Arg Leu Glu Ala Glu Asp Glu Gly Val Pro Ser Thr
35 40 45

Ala Ile Arg Glu Ile Ser Leu Leu Lys Glu Met Asn Asp Pro Asn Ile
50 55 60

Val Arg Leu Leu Asn Ile Val His Ala Asp Gly His Lys Leu Tyr Leu
65 70 75 80

Val Phe Glu Phe Leu Asp Leu Asp Leu Lys Lys Tyr Met Glu Ala Leu
85 90 95

Pro Val Ser Glu Gly Gly Arg Gly Arg Ala Leu Pro Asp Gly Ser Thr
100 105 110

Leu Ser Arg Asn Leu Gly Leu Gly Asp Ala Met Val Lys Lys Phe Met
115 120 125

Ala Gln Leu Ile Glu Gly Ile Arg Phe Cys His Ser His Arg Val Leu
130 135 140

His Arg Asp Leu Lys Pro Gln Asn Leu Leu Ile Asp Arg Asp Gly Asn
145 150 155 160

Leu Lys Leu Ala Asp Phe Gly Leu Ala Arg Ala Phe Gly Val Pro Leu
165 170 175

Arg Thr Tyr Thr His Glu Val Val Thr Leu Trp Tyr Arg Ser Pro Glu
180 185 190

Ile Leu Leu Gly Gly Arg Gln Tyr Ser Thr Gly Val Asp Met Trp Ser
195 200 205

Cys Gly Ala Ile Phe Ala Glu Met Cys Thr Arg Lys Pro Leu Phe Pro
210 215 220

```
Gly Asp Ser Glu Ile Asp Glu Ile Phe Lys Ile Phe Arg Ile Leu Gly
225                 230                 235                 240

Thr Pro Asp Glu Thr Ile Trp Pro Gly Val Thr Ser Phe Pro Asp Phe
                245                 250                 255

Lys Pro Thr Phe Pro Lys Trp Lys Arg Glu Asp Ile Gln Asn Val Val
            260                 265                 270

Pro Gly Leu Glu Glu Asp Gly Leu Asp Leu Leu Glu Ala Leu Leu Glu
        275                 280                 285

Tyr Asp Pro Ala Arg Arg Ile Ser Ala Lys Gln Ala Cys Met His Pro
    290                 295                 300

Tyr Phe Gln His Gly Ser Ser Tyr Tyr Ser Gly Arg Ala Arg Arg Asn
305                 310                 315                 320

Gly Phe His
```

( 2 ) INFORMATION FOR SEQ ID NO:22:

( i ) SEQUENCE CHARACTERISTICS:
( A ) LENGTH: 297 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:22:

```
Met Glu Asn Tyr Gln Lys Val Glu Lys Ile Gly Glu Gly Thr Tyr Gly
 1               5                  10                  15

Val Val Tyr Lys Ala Arg His Lys Leu Ser Gly Arg Ile Val Ala Met
            20                  25                  30

Lys Lys Ile Arg Leu Glu Asp Glu Ser Glu Gly Val Pro Ser Thr Ala
        35                  40                  45

Ile Arg Glu Ile Ser Leu Leu Lys Glu Val Asn Asp Glu Asn Asn Arg
    50                  55                  60

Ser Asn Cys Val Arg Leu Leu Asp Ile Leu His Ala Glu Ser Lys Leu
65                  70                  75                  80

Tyr Leu Val Phe Glu Phe Leu Asp Met Asp Leu Lys Lys Tyr Met Asp
                85                  90                  95

Arg Ile Ser Glu Thr Gly Ala Thr Ser Leu Asp Pro Arg Leu Val Gln
            100                 105                 110

Lys Phe Thr Tyr Gln Leu Val Asn Gly Val Asn Phe Cys His Ser Arg
        115                 120                 125

Arg Ile Ile His Arg Asp Leu Lys Pro Gln Asn Leu Leu Ile Asp Lys
    130                 135                 140

Glu Gly Asn Leu Lys Leu Ala Asp Phe Gly Leu Ala Arg Ser Phe Gly
145                 150                 155                 160

Val Pro Leu Arg Asn Tyr Thr His Glu Ile Val Thr Leu Trp Tyr Arg
                165                 170                 175

Ala Pro Glu Val Leu Leu Gly Ser Arg His Tyr Ser Thr Gly Val Asp
            180                 185                 190

Ile Trp Ser Val Gly Cys Ile Phe Ala Glu Met Ile Arg Arg Ser Pro
        195                 200                 205

Leu Phe Pro Gly Asp Ser Glu Ile Asp Glu Ile Phe Lys Ile Phe Gln
    210                 215                 220

Val Leu Gly Thr Pro Asn Glu Glu Val Trp Pro Gly Val Thr Leu Leu
225                 230                 235                 240

Gln Asp Tyr Lys Ser Thr Phe Pro Arg Trp Lys Arg Met Asp Leu His
```

| | | | | | | | | | | | | | | | |
|---|---|---|---|---|---|---|---|---|---|---|---|---|---|---|---|
| | | | | 245 | | | | | 250 | | | | | 255 | |
| Lys | Val | Val | Pro | Asn | Gly | Glu | Glu | Asp | Ala | Ile | Glu | Leu | Leu | Ser | Ala |
| | | | 260 | | | | | 265 | | | | | 270 | | |
| Met | Leu | Val | Tyr | Asp | Pro | Ala | His | Arg | Ile | Ser | Ala | Lys | Arg | Ala | Leu |
| | | 275 | | | | | 280 | | | | | 285 | | | |
| Gln | Gln | Asn | Tyr | Leu | Arg | Asp | Phe | His | | | | | | | |
| | 290 | | | | | 295 | | | | | | | | | |

( 2 ) INFORMATION FOR SEQ ID NO:23:

( i ) SEQUENCE CHARACTERISTICS:
( A ) LENGTH: 297 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:23:

| | | | | | | | | | | | | | | | |
|---|---|---|---|---|---|---|---|---|---|---|---|---|---|---|---|
| Met | Glu | Asp | Tyr | Ile | Lys | Ile | Glu | Lys | Ile | Gly | Glu | Gly | Thr | Tyr | Gly |
| 1 | | | | 5 | | | | | 10 | | | | | 15 | |
| Val | Val | Tyr | Lys | Gly | Arg | His | Arg | Thr | Thr | Gly | Gln | Ile | Val | Ala | Met |
| | | | 20 | | | | | 25 | | | | | 30 | | |
| Lys | Lys | Ile | Arg | Leu | Glu | Ser | Glu | Glu | Glu | Gly | Val | Pro | Ser | Thr | Ala |
| | | 35 | | | | | 40 | | | | | 45 | | | |
| Ile | Arg | Glu | Ile | Ser | Leu | Leu | Lys | Glu | Leu | Arg | His | Pro | Asn | Ile | Val |
| | 50 | | | | | 55 | | | | | 60 | | | | |
| Ser | Leu | Gln | Asp | Val | Leu | Met | Gln | Asp | Ser | Arg | Leu | Tyr | Leu | Ile | Phe |
| 65 | | | | | 70 | | | | | 75 | | | | | 80 |
| Glu | Phe | Leu | Ser | Met | Asp | Leu | Lys | Lys | Tyr | Leu | Asp | Ser | Ile | Pro | Pro |
| | | | | 85 | | | | | 90 | | | | | 95 | |
| Gly | Gln | Phe | Met | Asp | Ser | Ser | Leu | Val | Lys | Ser | Tyr | Leu | Tyr | Gln | Ile |
| | | | 100 | | | | | 105 | | | | | 110 | | |
| Leu | Gln | Gly | Ile | Val | Phe | Cys | His | Ser | Arg | Arg | Val | Leu | His | Arg | Asp |
| | | 115 | | | | | 120 | | | | | 125 | | | |
| Leu | Lys | Pro | Gln | Asn | Leu | Leu | Ile | Asp | Asp | Lys | Gly | Thr | Ile | Lys | Leu |
| | 130 | | | | | 135 | | | | | 140 | | | | |
| Ala | Asp | Phe | Gly | Leu | Ala | Arg | Ala | Phe | Gly | Ile | Pro | Ile | Arg | Val | Tyr |
| 145 | | | | | 150 | | | | | 155 | | | | | 160 |
| Thr | His | Glu | Val | Val | Thr | Leu | Trp | Tyr | Arg | Ser | Pro | Glu | Val | Leu | Leu |
| | | | | 165 | | | | | 170 | | | | | 175 | |
| Gly | Ser | Ala | Arg | Tyr | Ser | Thr | Pro | Val | Asp | Ile | Trp | Ser | Ile | Gly | Thr |
| | | | 180 | | | | | 185 | | | | | 190 | | |
| Ile | Phe | Ala | Glu | Leu | Ala | Thr | Lys | Lys | Pro | Leu | Phe | His | Gly | Asp | Ser |
| | | 195 | | | | | 200 | | | | | 205 | | | |
| Glu | Ile | Asp | Gln | Leu | Phe | Arg | Ile | Phe | Arg | Ala | Leu | Gly | Thr | Pro | Asn |
| | 210 | | | | | 215 | | | | | 220 | | | | |
| Asn | Glu | Val | Trp | Pro | Glu | Val | Glu | Ser | Leu | Gln | Asp | Tyr | Lys | Asn | Thr |
| 225 | | | | | 230 | | | | | 235 | | | | | 240 |
| Phe | Pro | Lys | Trp | Lys | Pro | Gly | Ser | Leu | Ala | Ser | His | Val | Lys | Asn | Leu |
| | | | | 245 | | | | | 250 | | | | | 255 | |
| Asp | Glu | Asn | Gly | Leu | Asp | Leu | Leu | Ser | Lys | Met | Leu | Val | Tyr | Asp | Pro |
| | | | 260 | | | | | 265 | | | | | 270 | | |
| Ala | Lys | Arg | Ile | Ser | Gly | Lys | Met | Ala | Leu | Lys | His | Pro | Tyr | Phe | Asp |
| | | 275 | | | | | 280 | | | | | 285 | | | |
| Asp | Leu | Asp | Asn | Gln | Ile | Lys | Lys | Met | | | | | | | |
| | 290 | | | | | 295 | | | | | | | | | |

( 2 ) INFORMATION FOR SEQ ID NO:24:

( i ) SEQUENCE CHARACTERISTICS:
( A ) LENGTH: 297 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:24:

Met Glu Asp Tyr Thr Lys Ile Glu Lys Ile Gly Glu Gly Thr Tyr Gly
1 5 10 15

Val Val Tyr Lys Gly Arg His Lys Thr Thr Gly Gln Val Val Ala Met
20 25 30

Lys Lys Ile Arg Leu Glu Ser Glu Glu Glu Gly Val Pro Ser Thr Ala
35 40 45

Ile Arg Glu Ile Ser Leu Leu Lys Glu Leu Arg His Pro Asn Ile Val
50 55 60

Ser Leu Gln Asp Val Leu Met Gln Asp Ser Arg Leu Tyr Leu Ile Phe
65 70 75 80

Glu Phe Leu Ser Met Asp Leu Lys Lys Tyr Leu Asp Ser Ile Pro Pro
85 90 95

Gly Gln Tyr Met Asp Ser Ser Leu Val Lys Ser Tyr Leu Tyr Gln Ile
100 105 110

Leu Gln Gly Ile Val Phe Cys His Ser Arg Arg Val Leu His Arg Asp
115 120 125

Leu Lys Pro Gln Asn Leu Leu Ile Asp Asp Lys Gly Thr Ile Lys Leu
130 135 140

Ala Asp Phe Gly Leu Ala Arg Ala Phe Gly Ile Pro Ile Arg Val Tyr
145 150 155 160

Thr His Glu Val Val Thr Leu Trp Tyr Arg Ser Pro Glu Val Leu Leu
165 170 175

Gly Ser Ala Arg Tyr Ser Thr Pro Val Asp Ile Trp Ser Ile Gly Thr
180 185 190

Ile Phe Ala Glu Leu Ala Thr Lys Lys Pro Leu Phe His Gly Asp Ser
195 200 205

Glu Ile Asp Gln Leu Phe Arg Ile Phe Arg Ala Leu Gly Thr Pro Asn
210 215 220

Asn Glu Val Trp Pro Glu Val Glu Ser Leu Gln Asp Tyr Lys Asn Thr
225 230 235 240

Phe Pro Lys Trp Lys Pro Gly Ser Leu Ala Ser His Val Lys Asn Leu
245 250 255

Asp Glu Asn Gly Leu Asp Leu Leu Ser Lys Met Leu Ile Tyr Asp Pro
260 265 270

Ala Lys Arg Ile Ser Gly Lys Met Ala Leu Asn His Pro Tyr Phe Asn
275 280 285

Asp Leu Asp Asn Gln Ile Lys Lys Met
290 295

( 2 ) INFORMATION FOR SEQ ID NO:25:

( i ) SEQUENCE CHARACTERISTICS:
( A ) LENGTH: 298 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:25:

```
Met Glu Asn Phe Gln Lys Val Glu Lys Ile Gly Glu Gly Thr Tyr Gly
1               5                   10                  15
Val Val Tyr Lys Ala Arg Asn Lys Leu Thr Gly Glu Val Val Ala Leu
            20                  25                  30
Lys Lys Ile Arg Leu Asp Thr Glu Thr Glu Gly Val Pro Ser Thr Ala
        35                  40                  45
Ile Arg Glu Ile Ser Leu Leu Lys Glu Leu Asn His Pro Asn Ile Val
    50                  55                  60
Lys Leu Leu Asp Val Ile His Thr Glu Asn Lys Leu Tyr Leu Val Phe
65                  70                  75                  80
Glu Phe Leu His Gln Asp Leu Lys Lys Phe Met Asp Ala Ser Ala Leu
                85                  90                  95
Thr Gly Ile Pro Leu Pro Leu Ile Lys Ser Tyr Leu Phe Gln Leu Leu
            100                 105                 110
Gln Gly Leu Ala Phe Cys His Ser His Arg Val Leu His Arg Asp Leu
        115                 120                 125
Lys Pro Gln Asn Leu Leu Ile Asn Thr Glu Gly Ala Ile Lys Leu Ala
    130                 135                 140
Asp Phe Gly Leu Ala Arg Ala Phe Gly Val Pro Val Arg Thr Tyr Thr
145                 150                 155                 160
His Glu Val Val Thr Leu Trp Tyr Arg Ala Pro Glu Ile Leu Leu Gly
                165                 170                 175
Ser Lys Tyr Tyr Ser Thr Ala Val Asp Ile Trp Ser Leu Gly Cys Ile
            180                 185                 190
Phe Ala Glu Met Val Thr Arg Arg Ala Leu Phe Pro Gly Asp Ser Glu
        195                 200                 205
Ile Asp Gln Leu Phe Arg Ile Phe Arg Thr Leu Gly Thr Pro Asp Glu
    210                 215                 220
Val Val Trp Pro Gly Val Thr Ser Met Pro Asp Tyr Lys Pro Ser Phe
225                 230                 235                 240
Pro Lys Trp Ala Arg Gln Asp Phe Ser Lys Val Val Pro Pro Leu Asp
                245                 250                 255
Glu Asp Gly Arg Ser Leu Leu Ser Gln Met Leu His Tyr Asp Pro Asn
            260                 265                 270
Lys Arg Ile Ser Ala Lys Ala Ala Leu Ala His Pro Phe Phe Gln Asp
        275                 280                 285
Val Thr Lys Pro Val Pro His Leu Arg Leu
    290                 295
```

( 2 ) INFORMATION FOR SEQ ID NO:26:

( i ) SEQUENCE CHARACTERISTICS:
( A ) LENGTH: 294 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:26:

```
Met Glu Gln Tyr Glu Lys Glu Glu Lys Ile Gly Glu Gly Thr Tyr Gly
1               5                   10                  15
Val Val Tyr Arg Ala Arg Asp Lys Val Thr Asn Glu Thr Ile Ala Leu
            20                  25                  30
```

-continued

| | | | | | | | | | | | | | | | |
|---|---|---|---|---|---|---|---|---|---|---|---|---|---|---|---|
| Lys | Lys | Ile | Arg | Leu | Glu | Gln | Glu | Asp | Glu | Gly | Val | Pro | Ser | Thr | Ala |
| | | 35 | | | | 40 | | | | | | 45 | | | |
| Ile | Arg | Glu | Ile | Ser | Leu | Leu | Lys | Glu | Met | His | His | Gly | Asn | Ile | Val |
| | 50 | | | | | 55 | | | | | 60 | | | | |
| Arg | Leu | His | Asp | Val | Ile | His | Ser | Glu | Lys | Arg | Ile | Tyr | Leu | Val | Phe |
| 65 | | | | | 70 | | | | | 75 | | | | | 80 |
| Glu | Tyr | Leu | Asp | Leu | Asp | Leu | Lys | Lys | Phe | Met | Asp | Ser | Cys | Pro | Glu |
| | | | | 85 | | | | | 90 | | | | | 95 | |
| Phe | Ala | Lys | Asn | Pro | Thr | Leu | Ile | Lys | Ser | Tyr | Leu | Tyr | Gln | Ile | Leu |
| | | | 100 | | | | | 105 | | | | | 110 | | |
| Arg | Gly | Val | Ala | Tyr | Cys | His | Ser | His | Arg | Val | Leu | His | Arg | Asp | Leu |
| | | 115 | | | | | 120 | | | | | 125 | | | |
| Lys | Pro | Gln | Asn | Leu | Leu | Ile | Asp | Arg | Arg | Thr | Asn | Ala | Leu | Lys | Leu |
| | 130 | | | | | 135 | | | | | 140 | | | | |
| Ala | Asp | Phe | Gly | Leu | Ala | Arg | Ala | Phe | Gly | Ile | Pro | Val | Arg | Thr | Phe |
| 145 | | | | | 150 | | | | | 155 | | | | | 160 |
| Thr | His | Glu | Val | Val | Thr | Leu | Trp | Tyr | Arg | Ala | Pro | Glu | Ile | Leu | Leu |
| | | | | 165 | | | | | 170 | | | | | 175 | |
| Gly | Ser | Arg | Gln | Tyr | Ser | Thr | Pro | Val | Asp | Met | Trp | Ser | Val | Gly | Cys |
| | | | 180 | | | | | 185 | | | | | 190 | | |
| Ile | Phe | Ala | Glu | Met | Val | Asn | Gln | Lys | Pro | Leu | Phe | Pro | Gly | Asp | Ser |
| | | 195 | | | | | 200 | | | | | 205 | | | |
| Glu | Ile | Asp | Glu | Leu | Phe | Lys | Ile | Phe | Arg | Val | Leu | Gly | Thr | Pro | Asn |
| | 210 | | | | | 215 | | | | | 220 | | | | |
| Glu | Gln | Ser | Trp | Pro | Gly | Val | Ser | Ser | Leu | Pro | Asp | Tyr | Lys | Ser | Ala |
| 225 | | | | | 230 | | | | | 235 | | | | | 240 |
| Phe | Pro | Lys | Trp | Gln | Ala | Gln | Asp | Leu | Ala | Thr | Ile | Val | Pro | Thr | Leu |
| | | | | 245 | | | | | 250 | | | | | 255 | |
| Asp | Pro | Ala | Gly | Leu | Asp | Leu | Leu | Ser | Lys | Met | Leu | Arg | Tyr | Glu | Pro |
| | | | 260 | | | | | 265 | | | | | 270 | | |
| Asn | Lys | Arg | Ile | Thr | Ala | Arg | Gln | Ala | Leu | Glu | His | Glu | Tyr | Phe | Lys |
| | | 275 | | | | | 280 | | | | | 285 | | | |
| Asp | Leu | Glu | Met | Val | Gln | | | | | | | | | | |
| | 290 | | | | | | | | | | | | | | |